United States Patent
Mc Gowan et al.

(10) Patent No.: US 11,597,704 B2
(45) Date of Patent: Mar. 7, 2023

(54) 2,4-DIAMINOQUINAZOLINE DERIVATIVES AND MEDICAL USES THEREOF

(71) Applicant: Janssen Sciences Ireland Unlimited Company, Co Cork (IE)

(72) Inventors: David Craig Mc Gowan, Brusssels (BE); Werner Constant Johan Embrechts, Beerse (BE); Jérôme Émile Georges Guillemont, Andé (FR); Ludwig Paul Cooymans, Beerse (BE); Tim Hugo Maria Jonckers, Heist-op-den Berg (BE); Pierre Jean-Marie Raboisson, Wavre (BE)

(73) Assignee: JANSSEN SCIENCES IRELAND UNLIMITED COMPANY, Co Cork (IE)

( * ) Notice: Subject to any disclaimer, the term of this patent is extended or adjusted under 35 U.S.C. 154(b) by 0 days.

(21) Appl. No.: 16/977,043

(22) PCT Filed: Feb. 28, 2019

(86) PCT No.: PCT/EP2019/054941
§ 371 (c)(1),
(2) Date: Aug. 31, 2020

(87) PCT Pub. No.: WO2019/166532
PCT Pub. Date: Sep. 6, 2019

(65) Prior Publication Data
US 2021/0040046 A1    Feb. 11, 2021

(30) Foreign Application Priority Data
Mar. 1, 2018 (EP) ..................................... 18159583

(51) Int. Cl.
*C07D 239/95* (2006.01)
(52) U.S. Cl.
CPC .................. *C07D 239/95* (2013.01)
(58) Field of Classification Search
CPC ... C07D 239/95; C07D 413/04; A61K 31/517
USPC .................. 544/284, 291; 514/266.23, 266.4
See application file for complete search history.

(56) References Cited

U.S. PATENT DOCUMENTS

| | | | |
|---|---|---|---|
| 6,028,076 | A | 2/2000 | Hirota et al. |
| 6,329,381 | B1 | 12/2001 | Kurimoto et al. |
| 6,376,501 | B1 | 4/2002 | Isobe et al. |
| 6,458,798 | B1 | 10/2002 | Fujita et al. |
| 6,503,908 | B1 | 1/2003 | Maw |
| 6,583,148 | B1 | 6/2003 | Kelley et al. |
| 6,951,866 | B2 | 10/2005 | Fujita et al. |
| 7,030,118 | B2 | 4/2006 | Lombardo et al. |

(Continued)

FOREIGN PATENT DOCUMENTS

| | | |
|---|---|---|
| CN | 101784548 A | 7/2010 |
| EP | 0882727 | 12/1998 |

(Continued)

OTHER PUBLICATIONS

Chawla et al.; CRIPS 5(1); 2004; p. 9, col. 2, para.1). (Year: 2004).*
Newman et al.; Drug Discovery Today 8(19); 2003; p. 898, col. 2, Para.3). (Year: 2003).*
O'Neill, et al.," I he History of Toll-Like Receptors—Redefining Innate Immunity", Nature Reviews, vol. 13; pp. 453-460 (Jun. 2013).
Abdillahi, et al., "Synthesis of a Novel Series of Thieno[3,2-d]pyrimidin-4-(3H)-ones", Synthesis, vol. 9: pp. 1428-1430 (2010).
Banker (Editor), "Prodrugs", Modern Pharmaceutics, Third Edition: pp. 596 (1976).
Baraldi, et al., "New Strategies for the Synthesis of A3 Adenosine Receptor Antagonists", Bioorganic & Medicinal Chemistry, vol. 11: pp. 4161-4169 (2003).

(Continued)

*Primary Examiner* — Jeffrey H Murray

(57) ABSTRACT

This application relates to quinazoline derivatives of formula (I), pharmaceutical compositions comprising the compounds of formula (I), and the use of the compounds of formula (I) in the treatment or prevention of a viral infection, of a virus-induced disease, of cancer or of an allergy. In formula (I), $R_1$ is a $C_{3-8}$alkyl, optionally substituted by one or more substituents independently selected from fluorine, hydroxyl, amino, nitrile, ester, amide, $C_{1-3}$ alkyl, or $C_{1-3}$ alkoxy, the carbon of $R_1$ bonded to the amine in the 4-position of the quinazoline is in (R)-configuration, $R_2$ is hydrogen, deuterium, fluorine, chlorine, methyl, methoxy, cyclopropyl, trifluoromethyl, or carboxylic amide, wherein each of methyl, methoxy and cyclopropyl is optionally substituted by one or more substituents independently selected from fluorine and nitrile, $R_3$ is hydrogen or deuterium, $R_4$ is hydrogen, deuterium, fluorine, methyl, carboxylic ester, carboxylic amide, nitrile, cyclopropyl, $C_{4-7}$ heterocycle, or 5-membered heteroaryl group, wherein each of methyl, cyclopropyl, $C_{4-7}$ heterocycle and 5-membered heteroaryl group is optionally substituted by one or more substituents independently selected from fluorine, hydroxyl, or methyl, $R_5$ is hydrogen, deuterium, fluorine, chlorine, methyl, or methoxy, provided that at least one of $R_2$, $R_3$, $R_4$ and $R_5$ is not hydrogen.

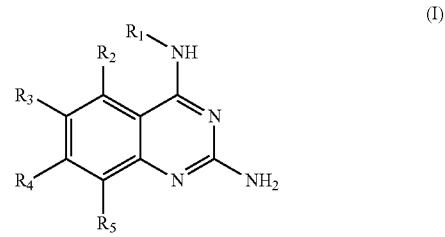

(I)

40 Claims, No Drawings

(56) References Cited

U.S. PATENT DOCUMENTS

| | | | |
|---|---|---|---|
| 7,091,232 B2 | 8/2006 | Chow et al. | |
| 7,498,409 B2 | 3/2009 | Vlach et al. | |
| 7,524,852 B2 | 4/2009 | Arai et al. | |
| 7,531,547 B2 | 5/2009 | Dillon et al. | |
| 7,754,728 B2 | 7/2010 | Isobe et al. | |
| 7,923,554 B2 | 4/2011 | Hoornaert et al. | |
| 3,012,964 A1 | 9/2011 | Kurimoto et al. | |
| 3,022,077 A1 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 * | 12/2014 | McGowan | A61P 29/00 514/266.1 |
| 9,133,192 B2 | 9/2015 | McGowan et al. | |
| 9,284,304 B2 | 3/2016 | McGowan et al. | |
| 9,365,571 B2 | 6/2016 | McGowan et al. | |
| 9,376,448 B2 | 6/2016 | Charifson et al. | |
| 9,416,114 B2 | 8/2016 | Gembus et al. | |
| 9,422,250 B2 | 8/2016 | Mc Gowan | |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2 | 3/2017 | McGowan et al. | |
| 9,663,474 B2 | 5/2017 | Last et al. | |
| 9,878,996 B2 | 1/2018 | Silverman et al. | |
| 10,377,738 B2 | 8/2019 | Mcgowan | |
| 2005/0054590 A1 | 3/2005 | Averett | |
| 2006/0258682 A1 | 11/2006 | Liao et al. | |
| 2007/0225303 A1 | 9/2007 | Ogita et al. | |
| 2008/0234251 A1 | 9/2008 | Doherty | |
| 2009/0285782 A1 | 11/2009 | Gao et al. | |
| 2010/0029585 A1 | 2/2010 | Howbert | |
| 2010/0143299 A1 | 6/2010 | Gao et al. | |
| 2014/0148433 A1 | 5/2014 | Follmann et al. | |
| 2015/0274676 A1 | 10/2015 | McGowan et al. | |
| 2015/0299221 A1 | 10/2015 | Bonfanti et al. | |
| 2015/0336907 A1 | 11/2015 | Gembus et al. | |
| 2016/0168150 A1 | 6/2016 | Mc Gowan | |
| 2016/0304531 A1 | 10/2016 | Bonfanti et al. | |
| 2019/0322678 A1 | 10/2019 | Jonckers | |

FOREIGN PATENT DOCUMENTS

| | | | | |
|---|---|---|---|---|
| EP | 0899263 A3 | | 3/1999 | |
| EP | 1552842 A1 | | 6/2003 | |
| EP | WO 2006050843 | * | 5/2006 | ........... C07D 239/42 |
| EP | 1110951 A1 | | 6/2006 | |
| EP | 1939198 A1 | | 7/2008 | |
| EP | 1970373 A1 | | 9/2008 | |
| EP | 2133353 A1 | | 12/2009 | |
| EP | 2138497 A1 | | 12/2009 | |
| EP | WO 2012156498 | * | 11/2012 | ........... C07D 239/95 |
| JP | 64063582 | | 3/1989 | |
| JP | 2000/053653 | | 2/2000 | |
| JP | 2000/053654 | | 2/2000 | |
| JP | 2008222557 A | | 9/2008 | |
| JP | 2009528989 A | | 8/2009 | |
| JP | 04342007 B2 | | 10/2009 | |
| JP | 2010522151 A | | 7/2010 | |
| JP | 2010532353 A | | 10/2010 | |
| WO | 199801448 A1 | | 1/1998 | |
| WO | 199808847 A1 | | 3/1998 | |
| WO | 199814448 A1 | | 4/1998 | |
| WO | 199850370 A1 | | 11/1998 | |
| WO | 199928321 A1 | | 6/1999 | |
| WO | 199932122 A1 | | 7/1999 | |
| WO | 199940091 A1 | | 8/1999 | |
| WO | 199941253 A1 | | 8/1999 | |
| WO | 200006577 A1 | | 2/2000 | |
| WO | 2000/61562 A1 | | 10/2000 | |
| WO | 2002087513 A2 | | 11/2002 | |
| WO | 2002088080 A2 | | 11/2002 | |
| WO | 2003/055890 A1 | | 7/2003 | |
| WO | 2004029054 A1 | | 8/2004 | |
| WO | 2005/007672 A2 | | 1/2005 | |
| WO | 2005092892 A1 | | 10/2005 | |
| WO | 2005092893 A1 | | 10/2005 | |
| WO | 2006015985 A1 | | 2/2006 | |
| WO | 2006/050843 A1 | | 5/2006 | |
| WO | 2006/117670 A1 | | 11/2006 | |
| WO | 2006120252 A2 | | 11/2006 | |
| WO | 2006122003 A3 | | 1/2007 | |
| WO | 2007034881 A1 | | 3/2007 | |
| WO | 2007056208 A1 | | 5/2007 | |
| WO | 2007063934 A1 | | 6/2007 | |
| WO | 2007/084413 A2 | | 7/2007 | |
| WO | 2007093901 A1 | | 8/2007 | |
| WO | 2008/009078 A2 | | 1/2008 | |
| WO | 2008/073785 A2 | | 6/2008 | |
| WO | 2008/075103 A1 | | 6/2008 | |
| WO | 2008/114008 A1 | | 9/2008 | |
| WO | 2008114817 A1 | | 9/2008 | |
| WO | 2008114819 A1 | | 9/2008 | |
| WO | 2008115319 A2 | | 9/2008 | |
| WO | 2008/147697 A1 | | 12/2008 | |
| WO | 2009/005687 A1 | | 1/2009 | |
| WO | 2009/023179 A2 | | 2/2009 | |
| WO | 2009030998 A1 | | 3/2009 | |
| WO | 2009/067081 A1 | | 5/2009 | |
| WO | 2009080836 A2 | | 7/2009 | |
| WO | 2009099650 A2 | | 8/2009 | |
| WO | 2009032668 A3 | | 9/2009 | |
| WO | 2009/134624 A1 | | 11/2009 | |
| WO | 2010006025 A1 | | 1/2010 | |
| WO | 2010007116 A3 | | 1/2010 | |
| WO | 2010/133885 A1 | | 11/2010 | |
| WO | 2011014535 A1 | | 2/2011 | |
| WO | 2011/049825 A1 | | 4/2011 | |
| WO | 2011049987 | | 4/2011 | |
| WO | 2011/062253 A1 | | 5/2011 | |
| WO | 2011/062372 A3 | | 5/2011 | |
| WO | 2012/066335 A1 | | 5/2012 | |
| WO | 2012067269 A1 | | 5/2012 | |
| WO | 2012045089 A3 | | 7/2012 | |
| WO | 2012/136834 A9 | | 10/2012 | |
| WO | 2012/156498 A1 | | 11/2012 | |
| WO | 2013/068438 A1 | | 5/2013 | |
| WO | 2013117615 A1 | | 8/2013 | |
| WO | 2014033170 A1 | | 3/2014 | |
| WO | 2014053595 A1 | | 4/2014 | |
| WO | 2014076221 A1 | | 5/2014 | |
| WO | 2014184350 A1 | | 11/2014 | |
| WO | 2016/141092 A1 | | 9/2016 | |
| WO | 2017140750 A1 | | 8/2017 | |
| WO | 2017181141 A2 | | 10/2017 | |
| WO | 2018/045144 A1 | | 3/2018 | |

OTHER PUBLICATIONS

Barker, et al., "A Rapid Conversion of 3-Oxothiolanes into 3-Aminothiophenes", Synthetic Communications, vol. 32(16): pp. 2565-2568 (2002).

Bell, et al., "Chemistry of 5-Pyrimidinecarboxaldehydes", Journal of Heterocyclic Chemistry, vol. 29: pp. 41-44 (Jan.-Feb. 1983).

Bennet, et al. (Editor), "Part XIV Oncology", Cecil Textbook of Medicine, vol. 1, 20th Edition: pp. 1004-1010 (1996).

Bizanek, et al., Isolation and Structure of an Intrastrand Cross-Link Adduct of Mitomycin C nd DNA, Biochemistry, 1992, pp. 3084-3091, vol. 31.

Brittain, et al., "Effects of Pharmaceutical Processing on Drug Polymorphs and Solvates", Polymorphism in Pharmaceutical Solids, 1999, pp. 331-360, Chapter 8.

Bruns, et al., "Solubilities of Adenosine Antagonists Determined by Radioreceptor Assay", Journal of Pharmacy and Pharmacology, vol. 41: pp. 590-594 (1989).

Chawla, et al., "Challenges in Polymorphism of Pharmaceuticals", Current Research & Information on Pharmaceutical Sciences, vol. 5(1): pp. 9-12 (Jan.-Mar. 2004).

De Clercq, et al., "(S)-9-(2,3-Dihydroxypropyl)adenine: An Aliphatic Nucleoside Analaog with Broad-Spectrum Antiviral Activity", Science, 1978, pp. 563-565, vol. 200.

(56) References Cited

OTHER PUBLICATIONS

De Nardo, "Toll-Like Receptors: Activation, Signalling and Transcriptional Modulation", Cytokine, 2015, pp. 181-189, vol. 74.
Dermer, "Another Anniversary for the War on Cancer", Bio/Technology, vol. 12: pp. 320 (Mar. 1994).
Douglas, Jr., "Introduction of Viral Diseases", Cecil Textbook of Medicine, 20th Edition, vol. 2: pp. 1973-1942 (1996).
Freshney, et al., Culture of Animal Cells, Manual of Basic Technique, 1983, pp. 1-6, Chapter 1.
Fried, et al., "Peginterferon Alfa-2a Plus Ribavirin for Chronic Hepatitis C Virus Infection", New England Journal of Medicine, Sep. 26, 2002, pp. 975-985, vol. 347 (13).
Grimm, et al., "Toll-like receptor (TLR) 7 and TLRS expression on CD133+ cells in colorectal cancer points to a specific raid for inflammation inducted TLRs in tumourigenesis and tumour progression", European Journal of Cancer, 2010, pp. 2849-2857, vol. 46.
Hackam, et al., "Translation of Research Evidence From animals to Humans", JAMA, vol. 296 (14): pp. 1731-1732 (2006).
Hoffmann, "The Immune Response of *Drosophila*", Nature, vol. 426: pp. 33-38 (Nov. 6, 2003).
Hood, et al., "Immunoprofiling toll-like receptor ligands Comparison of Immunostimulatory and proinflammatory profiles in ex vivo human blood models", Human Vaccines, vol. 6(4): pp. 322-335 (Apr. 2010).
Horscroft, et al., "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy- And 3-Amino-Thiophens From Derivatives of 2-Choroacrylic Acid", Synthetic Communications, vol. 9(8): pp. 731-734 (1979).
Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).
Isobe, et al., "Synthesis and Structure-Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).
Jakobsen, et al.,, " Synthesis of Heteromine C from Guanine", Heterocycles, vol. 53 (4); pp. 935-940 (2000).
Jiang, et al., "Synthesis of 4-chlorothieno[3,2-d]pyrimidine", Chemical Industry and Engineering Progress, vol. 30: pp. 2532-2535, (2011). [With English Abstract].
Jo, et al., "Toll-Like Receptor 8 Agonist and Bacteria Trigger Potent Activation of Innate Immune Cells in Human Liver", PLOS Pathogens, vol. 10 (6); pp. 1-13 e1004210 (Jun. 2014).
Jordan, "Tamoxifen: a Most Unlikely Pioneering Medicine", Nature Reviews, vol. 2: pp. 205-213, (Mar. 2003).
Jurk, et al., "Human TLR7 or TLR8 Independently Confer Responsiveness to the Antiviral Compound R-848", Mature Immunology, Jun. 2002, pp. 499, vol. 3 (6).
Kanzler, et al., "Therapeutic Targeting of Innate Immunity with Toll-Like Receptor Agonists and Antagonists", Nature Medicine, vol. 13(5): pp. 552-559 (May 2007).
Krieger, et al, Enhancement of Hepatitis C Virus RNA Replication by Cell Culture-Adaptive Mutations, Journal of Virology, May 2001, 4614-4624, 75/10.
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Lee, et al., "Activation of Anti-Hepatitis C Virus Responses via Toll-Like Receptor 7", PNAS, vol. 3 (6); pp. 1828-1833 (Feb. 7, 2006).
Liu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).

Lohmann et al., Viral and Cellular Determinants of Hepatitis C Virus RNA Replication in Cell Culture, Journal of Virology, Mar. 2003, pp. 3007-3019, vol. 77, No. 5.
Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
McGowan, et al., "Novel Pyrimidine Toll-Like Receptor 7 and 8 Dual Agonists to Treat Hepatitis B Virus", Journal of Medicinal Chemistry, vol. 59 (17); pp. 7936-7949 (2016).
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-222 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule interferon Inducers. Toward the Comprehension of the Molecular Determinants through Ligand-Based Approaches", J. Chem. Inf. Model., vol. 49: pp. 1777-1786 (2009).
Newman, et al., "Solid-State Analysis of the Active Pharmaceutical Ingredient in Drug Products", Drug Discovery Today, Oct. 19, 2003, pp. 898-905, vol. 8(19).
O'Hara, et al., "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).
Ohto, et al., "Structure and Function of Toll-Like Receptor 8", Microbes and Infections, vol. 16: pp. 273-282 (2014).
Online Registry via STN 1991-07-05, RN 134678-17-4.
Organic Syntheses Collective, "3-Methylcoumarone", Organic Syntheses Collective, 1963, pp. 43-46, vol. 4.
Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).
Schurich, et al., "The Third Signal Cytokine IL-12 Rescues the Anti-Viral Function of Exhausted HBV-Specific CD8 T Cells", PLOS Pathogens, vol. 9 (3); pp. 1-12 e1003208 (Mar. 2013).
Takeda, et al., "Toll-Like Receptors", Annu. Rev. Immunol, vol. 21: pp. 335-376 (2003).
Thomas, et al., "Investigating Toll-Like Receptor Agonists for Potential To Treat Hepatitis C Virus Infection", Antimicrobial Agents and Chemotherapy, vol. 51(8): pp. 2969-2978 (Aug. 2007).
Tomonori, et al., "Ti-Crossed-Claisen Condensation between Carboxylic Ester and Acid Chlorides or Acids: A Highly Selective and General Method for the Preparation of Various β-Keto Esters", Journal of the American Chemical Society, vol. 127:pp. 2854-2855 (2005).
Tran, et al., "Design and optimization of orally active TLR7 agonists for the treatment of hepatitis C virus infection", Bioorganic & Medicinal Chemistry Letters, vol. 21: pp. 2389-2393 (2011).
Ulevitch, "Therapeutics Targeting the Innate Immune System", Nature, vol. 4: pp. 512-520 (Jul. 2004).
Ulrich, et al, "Crystallization", Kirk-Othmer Encyclopedia of Chemical Technology, Chapter 4: pp. 1-63, (Aug. 16, 2002).
Vedantham, et al., "Mechanism of Interferon Action in Hairy Cell Leukemia: A Model of Effective Cancer Biotherapy", Cancer Research, vol. 52: pp. 1056-1066 (Mar. 1, 1992).
Vippagunta, et al., "Crystalline Solids", Advance Drug Delivery Reviews, vol. 48: pp. 3-26 (2001).
Wan, et al., "An Efficient Direct Amination of Cyclic Amides and Cyclic Ureas", Organic Letters, vol. 8(11); p. 2425-2428 (2006).
Warshakoon, et al., "Potential Adjuvantic Properties of Innate Immune Stimuli", Human Vaccines, vol. 5(6): pp. 381-394 (Jun. 2009).
Wermuth, "Molecular Variations Based on Isosteric Replacements", The Practice of Medicinal Chemistry, 1996, pp. 203-237, Ch. 13.

(56) References Cited

OTHER PUBLICATIONS

Wolff, et al., Burger's Medicinal Chemistry and Drug Discovery,—, 1995 pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu, et al., "Toll-Like Receptor 7 Agonists: Chemical Feature Based", Plos One, vol. 8 (3): pp. 1-11 e56514, (Mar. 20, 2013).
Yu, et al., "Dual Character of Toll-Like Receptor Signaling: Pro-Tumorigenic Effectsand Anti-Tumor Functions", Biochimica et Biophysica Acta, vol. 1835: pp. 144-154 (2013).
Zhao, et al., "Toll-Like Receptors and Prostate Cancer", Frontiers in Immunology, vol. 5 (Article 352): pp. 1-7 (Jul. 2014).
Kim, et al., "De Novo Design of 2-Amino-4-Alkylaminoquinazoline-7-Carboxamides as Potential Scaffold for JAK1-Selective Inhibitors", Bulletin of the Korean Chemical Society, vol. 35(11); pp. 3377-3380, (2014).
Pieters, et al., "Discovery of selective 2,4-diaminoquinazoline toll-like receptor 7 (TLR7) agonists", Bioorganic & Medicinal Chemistry Letters, vol. 28(4); pp. 711-719 (2018).
International Search Report and Written Opinion for PCT Application No. PCT/EP2019/054941 dated Apr. 15, 2019.

\* cited by examiner

2,4-DIAMINOQUINAZOLINE DERIVATIVES AND MEDICAL USES THEREOF

CROSS-REFERENCE TO RELATED APPLICATIONS

This application is a national phase entry of International Application No. PCT/EP2019/054941, filed on Feb. 28, 2019, which claims priority to EP Patent Application No. 18159583.6, filed on Mar. 1, 2018, each of which is incorporated herein in its entirety.

FIELD

The application describes quinazoline derivatives, processes for their preparation, pharmaceutical compositions, and medical uses thereof, more particularly in the filed of therapy. The means described in the application are suitable for modulating, more particularly agonising, Toll-Like-Receptors (TLRs), more particularly TLR8. The means described in the application are notably useful in the treatment or prevention of diseases or conditions, such as viral infections, immune or inflammatory disorders.

BACKGROUND

Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behavior.

It has been estimated that most mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

In the treatment of certain ailments, it may be advantageous to induce IL-12, or IFNγ, among other cytokines by agonizing the TLR 7/8 receptors (Schurich et. al PLoS Pathology 2013, 9, e1003208 and Jo, J et. al PLoS Pathology 2014, 10, e1004210).

For reviews on toll-like receptors see the following journal articles. Hoffmann, J. A., Nature, 426, p33-38, 2003; Akira, S., Takeda, K., and Kaisho, T., Annual Rev. Immunology, 21, p335-376, 2003; Ulevitch, R. J., Nature Reviews: Immunology, 4, p512-520, 2004. O'Neil et. al Nature Reviews Immunology 13, 453-460, 2013. Compounds indicating activity on Toll-Like receptors have been previously described such as WO2006117670, WO98/01448, WO9928321, WO 2009067081, WO2012136834, WO2012156498, WO2014076221 and WO2016141092.

There exists a strong need for novel Toll-Like receptor modulators having preferred selectivity, and an improved safety profile compared to the compounds of the prior art.

SUMMARY

The application provides a compound of formula (I)

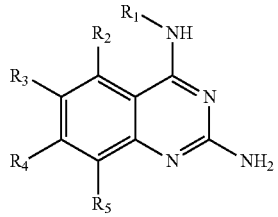

or a pharmaceutically acceptable salt, solvate or polymorph thereof, wherein $R_1$ is a $C_{3-8}$alkyl, optionally substituted by one or more substituents (more particularly 1, 2 or 3 substituents, more particularly 1 or 2 substituents, more particularly 1 substituent) independently selected from fluorine, hydroxyl, amino, nitrile, ester, amide, $C_{1-3}$alkyl, or $C_{1-3}$alkoxy, the carbon of $R_1$ bonded to the amine in the 4-position of the quinazoline is in (R)-configuration, $R_2$ is hydrogen, deuterium, fluorine, chlorine, methyl, methoxy, cyclopropyl, trifluoromethyl, or carboxylic amide, wherein each of methyl, methoxy and cyclopropyl is optionally substituted by one or more substituents (more particularly one substituent) independently selected from fluorine and nitrile, $R_3$ is hydrogen or deuterium, $R_4$ is hydrogen, deuterium, fluorine, methyl, carboxylic ester, carboxylic amide, nitrile, cyclopropyl, $C_{4-7}$heterocycle, or 5-membered heteroaryl group, wherein each of methyl, cyclopropyl, $C_{4-7}$heterocycle and 5-membered heteroaryl group is optionally substituted by one or more substituents (more particularly 1 or 2 substituents, more particularly 1 substituent) independently selected from fluorine, hydroxyl and methyl, and $R_5$ is hydrogen, deuterium, fluorine, chlorine, methyl, or methoxy, provided that at least one of $R_2$, $R_3$, $R_4$ and $R_5$ is not hydrogen.

The products of the application may advantageously display improved TLR8 agonism (or selectivity) over TLR7.

The application also provides means, which comprise or contains the compound of the application, such as pharmaceutical composition, immunological compositions and kits.

The products and means of the application may be useful in the activation or stimulation of TLR8.

The products and means of the application may be useful in the activation or stimulation of a Th1 immune response and/or of the production of cytokines, such as IL12.

The products and means of the application are notably useful in the treatment or prevention of virus infection or of a virus-induced disease, more particularly of an HBV infection or of an HBV-induced disease, as well as in other

DETAILED DESCRIPTION

The application describes the subject matter described below, the subject illustrated below as well the subject matter defined in the claims as filed, which are herein incorporated by reference.

The application provides a compound of formula (I)

<chemical structure: formula (I) - quinazoline with R1-NH at 4-position, R2, R3, R4, R5 substituents, and NH2 at 2-position> or a pharmaceutically acceptable salt, solvate or polymorph thereof, wherein $R_1$ is a $C_{3-8}$alkyl, optionally substituted by one or more substituents (more particularly 1, 2 or 3 substituents, more particularly 1 or 2 substituents, more particularly 1 substituent) independently selected from fluorine, hydroxyl, amino, nitrile, ester, amide, $C_{1-3}$alkyl, or $C_{1-3}$alkoxy, the carbon of $R_1$ bonded to the amine in the 4-position of the quinazoline is in (R)-configuration, $R_2$ is hydrogen, deuterium, fluorine, chlorine, methyl, methoxy, cyclopropyl, trifluoromethyl, or carboxylic amide wherein each of methyl, methoxy and cyclopropyl is optionally substituted by one or more substituents (more particularly one substituent) independently selected from fluorine, or nitrile, $R_3$ is hydrogen or deuterium, $R^4$ is hydrogen, deuterium, fluorine, methyl, carboxylic ester, carboxylic amide, nitrile, cyclopropyl, $C_{4-7}$heterocycle, or 5-membered heteroaryl group, wherein each of methyl, cyclopropyl, $C_{4-7}$heterocycle and 5-membered heteroaryl group is optionally substituted by one or more substituents (more particularly 1 or 2 substituents, more particularly 1 substituent) independently selected from fluorine, hydroxyl, or methyl, and $R_5$ is hydrogen, deuterium, fluorine, chlorine, methyl, or methoxy, provided that at least one of $R_2$, $R_3$, $R_4$ and $R_5$ is not hydrogen (i.e., $R_2$, $R_3$, $R_4$ and $R_5$ cannot all be H at the same time).

$R_4$ can be of (R) or (S) configuration.

The products of the application may advantageously display improved TLR8 agonism (or selectivity) over TLR7.

TLR 7/8 agonists are also of interest as vaccine adjuvants because of their ability to induce a Th1 response. TLR8 agonists are of particular interest to affect the induction of IL12 as well as other cytokines.

In general, it may be advantageous for the compounds of formula (I) to have low metabolic stability, or to be otherwise rapidly cleared thus limiting the concentration in systemic circulation and immune overstimulation that may lead to undesired effects.

Unless specified otherwise or unless a context dictates otherwise, all the terms have their ordinary meaning in the relevant field(s).

The term "alkyl" refers to a straight-chain or branched-chain saturated aliphatic hydrocarbon containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

Heterocycle refers to molecules that are saturated or partially saturated and include, tetrahydrofuran, oxetane, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Heteroaryl groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, oxadiazolyl, oxazolyl, pyrrolyl, pyridonyl, pyridyl, pyridazinyl, pyrazinyl, Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the application may also exist in unsolvated and solvated forms.

The term "solvate" is used herein to describe a molecular complex comprising the compound of the application and one or more pharmaceutically acceptable solvent molecules, for example, ethanol.

The term "polymorph" refers to the ability of the compound of the application to exist in more than one form or crystal structure.

In embodiments, the application provides compounds of formula (I) wherein $R_1$ is a $C_{4-8}$ alkyl substituted with a hydroxyl, and wherein $R_2$, $R_3$, $R_4$ and $R_5$ are as specified above.

In embodiments, the application provides compounds of formula (I) wherein $R_1$ is of formula (II):

<chemical structure: formula (II) - CH2OH attached to (R)-configured carbon with chain (CH2)n where n = 0, 1 or 2, more particularly 1> or of formula (III):

<chemical structure: formula (III) - CH2OH attached to (R)-configured carbon with chain (CH2)n where n = 0, 1 or 2, more particularly 1> or of formula (IV):

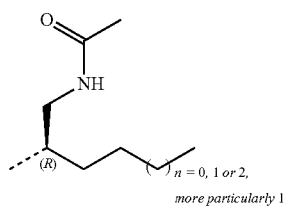

formula (IV)

or of formula (V):

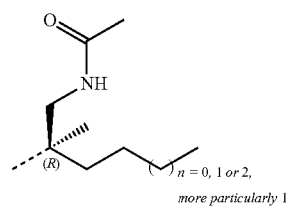

formula (V)

and wherein $R_2$, $R_3$, $R_4$ and $R_5$ are as specified above.

In embodiments, the application provides compounds of formula (I) wherein $R_2$ is fluorine, chlorine or methyl, and wherein methyl is optionally substituted by one or more substituents independently selected from fluorine and nitrile, and wherein $R_1$, $R_3$, $R_4$ and $R_5$ are as described above.

In embodiments, the application provides compounds of formula (I) wherein $R_2$ is fluorine, chlorine or methyl, and wherein methyl is optionally substituted by one or more substituents independently selected from fluorine and nitrile, and wherein $R_1$ is of formula (II), (III), (IV) or (V), more particularly of formula (II) or (III), more particularly of formula (II), and wherein $R_3$, $R_4$ and $R_5$ are as described above.

In embodiments, the application provides compounds of formula (I) wherein $R_2$ is fluorine or chlorine, more particularly fluorine, and wherein $R_1$, $R_3$, $R_4$ and $R_5$ are as described above.

In embodiments, the application provides compounds of formula (I) wherein $R_2$ is fluorine or chlorine, more particularly fluorine, wherein $R_1$ is of formula (II), (III), (IV) or (V), more particularly of formula (II) or (III), more particularly of formula (II), and wherein $R_3$, $R_4$ and $R_5$ are as described above.

In embodiments, the application provides compounds of formula (I) wherein $R_5$ is fluorine or chlorine, more particularly fluorine, and wherein $R_1$, $R_2$, $R_3$ and $R_4$ are as described above.

In embodiments, the application provides compounds of formula (I) wherein $R_5$ is fluorine or chlorine, more particularly fluorine, wherein $R_1$ is of formula (II), (III), (IV) or (V), more particularly of formula (II) or (III), more particularly of formula (II), and wherein $R_2$, $R_3$ and $R_4$ are as specified above.

In embodiments, the application provides compounds of formula (I) wherein $R_4$ is fluorine or methyl, more particularly fluorine, and wherein methyl is optionally substituted by one or more substituents independently selected from fluorine, hydroxyl, or methyl, and wherein $R_1$, $R_2$, $R_3$ and $R_5$ are as described above.

In embodiments, the application provides compounds of formula (I) wherein $R_4$ is fluorine or methyl, more particularly fluorine, and wherein methyl is optionally substituted by one or more substituents independently selected from fluorine, hydroxyl, or methyl, and wherein of formula (II), (III), (IV) or (V), more particularly of formula (II) or (III), more particularly of formula (II), and wherein $R_2$, $R_3$ and $R_5$ are as specified above.

In embodiments, the application provides compounds of formula (I) wherein $R_4$ is fluorine or chlorine, more particularly fluorine, and wherein $R_1$, $R_2$, $R_3$ and $R_5$ are as described above.

In embodiments, the application provides compounds of formula (I) wherein $R_4$ is fluorine or chlorine, more particularly fluorine, wherein $R_1$ is of formula (II), (III), (IV) or (V), more particularly of formula (II) or (III), more particularly of formula (II), and wherein $R_2$, $R_3$ and $R_5$ are as specified above.

In embodiments, the application provides compounds of formula (I) wherein $R_2$ is fluorine, chlorine, methyl, more particularly fluorine, wherein $R_4$ is fluorine or chlorine, more particularly fluorine, wherein of formula (II), (III), (IV) or (V), more particularly of formula (II) or (III), more particularly of formula (II), and wherein $R_3$ and $R_5$ are as specified above.

In embodiments, the application provides compound number 1 to compound number 34 (compounds 1-34) as described in Table 5 below.

TABLE 5

| Compound number | |
|---|---|
| 1 | ![structure with cyclopropyl, OH, HN, (R), N, NH2] |
| 2 | ![structure with F, OH, HN, (R), N, NH2] |
| 3 | ![structure with CF3, OH, HN, (R), N, NH2] |

TABLE 5-continued
| Compound number | |
|---|---|
| 4 | 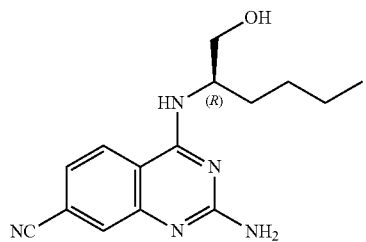 |
| 5 | 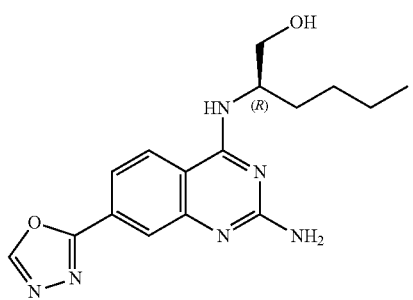 |
| 6 | 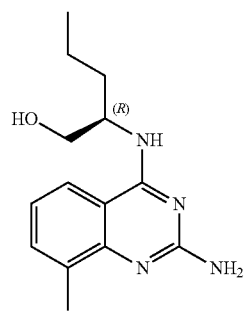 |
| 7 | 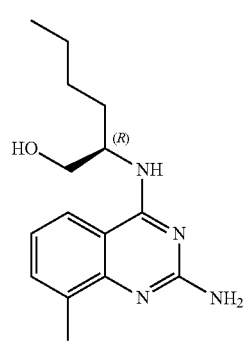 |
| 8 | 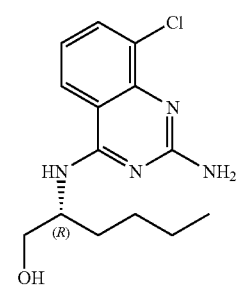 |
| 9 | 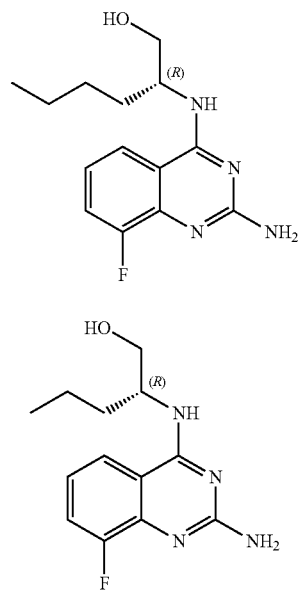 |
| 10 | 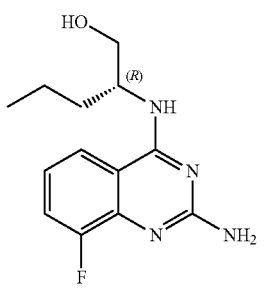 |
| 11 | 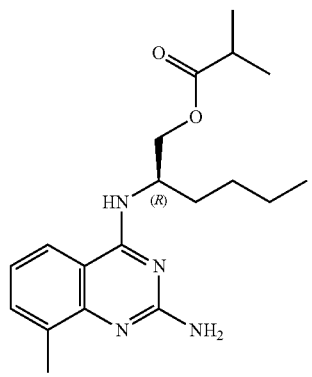 |
| 12 | 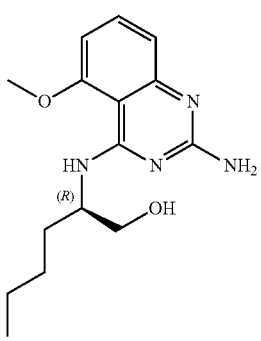 |

TABLE 5-continued

| Compound number | Structure |
|---|---|
| 13 | 2-amino-7-fluoro-N-[(R)-1-(hydroxymethyl)pentyl]quinazolin-4-amine |
| 14 | 2-amino-N-[(R)-1-(hydroxymethyl)pentyl]-7-methylquinazolin-4-amine |
| 15 | 2-amino-5-chloro-N-[(R)-1-(hydroxymethyl)pentyl]quinazolin-4-amine |
| 16 | 2-amino-N-[(R)-1-(hydroxymethyl)pentyl]-5-methylquinazolin-4-amine |
| 17 | 2-amino-N-[(R)-1-(hydroxymethyl)pentyl]-8-methoxyquinazolin-4-amine |
| 18 | methyl 2-amino-4-{[(R)-1-(hydroxymethyl)pentyl]amino}quinazoline-7-carboxylate |
| 19 | 2-amino-7,8-difluoro-N-[(R)-1-(hydroxymethyl)pentyl]quinazolin-4-amine |
| 20 | 2-amino-5-fluoro-N-[(R)-1-(hydroxymethyl)-3-(methylthio)propyl]quinazolin-4-amine |
| 21 | 2-amino-5-fluoro-N-[(1R,2S)-1-(hydroxymethyl)-2-methylbutyl]quinazolin-4-amine |
| 22 | 2-amino-4-{[(R)-1-(hydroxymethyl)pentyl]amino}-N-methylquinazoline-5-carboxamide |
| 23 | 2-amino-5,7-difluoro-N-[(R)-1-(hydroxymethyl)pentyl]quinazolin-4-amine |

TABLE 5-continued

| Compound number | Structure |
|---|---|
| 24 | (R)-2-((2-aminoquinazolin-4-yl)amino)-7-(trifluoromethyl) hexanol structure |
| 25 | (R)-N,N-dimethyl-4-((1-hydroxyhexan-2-yl)amino)-2-aminoquinazoline-7-carboxamide structure |
| 26 | (R)-2-((2-amino-5-fluoro-8-methylquinazolin-4-yl)amino)hexan-1-ol structure |
| 27 | (R)-2-((2-amino-5-fluoroquinazolin-4-yl)amino)-2-methylhexan-1-ol structure |
| 28 | (R)-2-((2-amino-5-fluoroquinazolin-4-yl)amino)-2,4-dimethylpentan-1-ol structure |
| 29 | (2S,3R)-3-((2-amino-5-fluoroquinazolin-4-yl)amino)hexane-1,2-diol structure |
| 30 | (2R,3R)-3-((2-amino-5-fluoroquinazolin-4-yl)amino)hexane-1,2-diol structure |
| 31 | (R)-2-((2-amino-5-fluoroquinazolin-4-yl)amino)-3-methylhexan-1-ol structure |
| 32 | (2R,3S)-2-((2-amino-5-fluoroquinazolin-4-yl)amino)-3-methylhexan-1-ol structure |
| 33 | (R)-N-(1-methoxyhexan-2-yl)-2-amino-5-fluoroquinazolin-4-amine structure |
| 34 | (R)-2-((2-amino-5-fluoroquinazolin-4-yl)amino)hex-5-en-1-ol structure |

In embodiments, the application provides compounds 1, 2, 3, 4, 5, 7, 9, 11, 12, 13, 14, 15, 16, 18, 19, 20, 21, 22, 23, 24 and 26 (as described e.g., in Table 5).

In embodiments, the application provides compounds 1, 2, 3, 4, 5, 7, 9, 11, 12, 13, 14, 15, 16, 18, 19, 20, 21, 23, 24 and 26 (as described e.g., in Table 5).

In embodiments, the application provides compounds 2, 13, 14, 15, 16, 21 and 23 (as described e.g., in Table 5).

In embodiments, the application provides compounds 2, 13, 15, 21 and 23 (as described e.g., in Table 5).

In an embodiment, the application provides compound 2 (as described e.g., in Table 5).

In an embodiment, the application provides compound 13 (as described e.g., in Table 5).

In an embodiment, the application provides compound 15 (as described e.g., in Table 5).

In an embodiment, the application provides compound 16 (as described e.g., in Table 5).

In an embodiment, the application provides compound 21 (as described e.g., in Table 5).

In an embodiment, the application provides compound 23 (as described e.g., in Table 5).

The compounds of the application and their pharmaceutically acceptable salt, solvate or polymorph thereof have activity as pharmaceuticals, in particular as modulators of TLR7 and/or TLR8 activity, more particularly of TLR8 activity.

The term "modulator" includes both inhibitor and activator, where inhibitor refers to compounds that decrease or inactivate the activity of the receptor, and where activator refers to compounds that increase or activate the activity of the receptor. More particularly, the compounds of the application and their pharmaceutically acceptable salt, solvate or polymorph thereof may have activity agonists of TLR7 and/or TLR8 activity, more particularly of TLR8 activity.

The products of the application may advantageously display improved TLR8 agonism (or selectivity) over TLR7. Alternatively or complementarily, the products of the application may advantageously display improved TLR8 agonism compared to the compounds described in WO2012156498.

Means for determining TLR7 activity and/or TLR8 activity, more particularly TLR8 activity, are known to the person of ordinary skill in the art. Means for determining TLR7 activity and/or TLR8 activity, more particularly TLR8 activity, may comprise cells that have been genetically engineered to express TLR7 or TLR8, such as the NF-κB reporter (luc)-HEK293 cell line.

TLR7 or TLR8 activity can be expressed as the lowest effective concentration (LEC) value, i.e., the concentration that induces an effect which is at least two-fold above the standard deviation of the assay.

The products of the application may advantageously stimulate or activate cytokine production (or secretion), more particularly the production of IL12 (in a mammal).

The application provides a pharmaceutical composition, or an immunological composition, or a vaccine, comprising a compound of the application or a pharmaceutically acceptable salt, solvate or polymorph thereof, together with one or more pharmaceutically acceptable excipients, diluents or carriers.

A compound of the application or a pharmaceutically acceptable salt, solvate or polymorph thereof, or a pharmaceutical composition of the application, can be used as a medicament.

A compound of the application or a pharmaceutically acceptable salt, solvate or polymorph thereof, or a pharmaceutical composition of the application, can be used as a vaccine adjuvant or as an immunomodulator, notably to activate or stimulate a Th1 response and/or to stimulate or activate the production of one or more cytokines, more particularly IL12.

A compound of the application or a pharmaceutically acceptable salt, solvate or polymorph thereof, or a pharmaceutical composition of the application, may be used in the treatment or prevention of a disease or disorder in which the modulation of TLR7 and/or TLR8, more particularly TLR8, is involved.

Such diseases or conditions may notably encompass viral infection, virus-induced diseases, (virally induced or not virus-induced) cancer and allergy, more particularly viral infection, (virally induced or non-virally induced) virus-induced diseases and cancer, more particularly viral infection and virus-induced diseases.

Such diseases or conditions may notably encompass viral infection, more particularly chronic viral infection, as well as (virally-induced or non-virally induced) tumors, more particularly malignant tumors or cancer.

Such diseases or conditions encompass more particularly viral infection, more particularly HBV infection, more particularly chronic HBV infection.

Such diseases or conditions encompass more particularly virally-induced diseases (or disorders), more particularly HBV-induced diseases (or disorders).

Such diseases or conditions encompass more particularly one or several diseases (or disorders) chosen from among liver fibrosis, liver inflammation, liver necrosis, cirrhosis, liver disease, and hepatocellular carcinoma.

Such diseases or conditions encompass more particularly (virally-induced or non-virally induced) tumors, more particularly malignant tumors or cancer.

Such diseases or conditions encompass more particularly allergy.

The term "mammal" encompasses non-human mammals as well as humans. Non-human mammals notably comprise ovine, bovine, porcine, canine, feline, rodent and murine mammals, as well as non-human primates. The term "human(s)" encompasses more particularly human(s) who is(are) HBV infected, more particularly which has(have) a chronic HBV infection.

The term "treatment" is not limited to the meaning of curative treatment, but includes any treatment that the person of average skill in the art or the skilled physician would contemplate as therapy or as part of a therapy. The term "treatment" may thus includes amelioration treatment, palliative treatments, remission treatment.

The products of the application may advantageously show improved clearance (from the mammal systemic circulation), notably compared to prior art TLR7 and/or TLR8 agonists.

The compounds of the application may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the application or in combination with one or more other drugs. Generally, they will be administered as a formulation in association with one or more pharmaceutically acceptable excipients.

The term "excipient" is used herein to describe any ingredient other than the compound(s) of the application. The choice of excipient depends largely on factors such as the mode of administration, the effect of the excipient on solubility and stability, and the nature of the dosage form.

The compounds of the application or any subgroup thereof may be formulated into various pharmaceutical forms for administration purposes. As appropriate compositions, there may be cited all compositions usually employed for systemically administering drugs. To prepare the pharmaceutical compositions of the application, an effective amount of the compound, optionally in salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In a composition suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the application may also be administered via inhalation or insufflation by means of methods and formulations employed in the art for administration via this way. Thus, in general the compounds of the application may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of average skill in the treatment of infectious diseases will be able to determine the effective amount for administration in an individual in need thereof. In general, it is contemplated that an effective daily amount would be from 0.01 mg/kg to 200 mg/kg body weight. It may be appropriate to administer the required dose as two, three, four or more sub-doses at appropriate intervals throughout the day. Said sub-doses may be formulated as unit dosage forms, for example, containing 0.1 to 1000 mg, and in particular, 1 to 200 mg of active ingredient per unit dosage form. It may also be appropriate to administer the required dose on a less frequent basis, for example, once or twice weekly, or infrequently on a monthly basis.

An effective amount can be the amount that is sufficient to stimulate or activate (the activity of) TLR8 receptor, or of TLR8 and TLR7 receptors.

An effective amount can be the amount that is sufficient to stimulate or activate cytokine production (or secretion), more particularly L12.

The exact dosage and frequency of administration depends on the compound used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the application. The effective amount ranges mentioned above are therefore only guidelines and are not intended to limit the scope or use of the application to any extent.

The application also provides a product, or kit, comprising a first compound and a second compound as a combined preparation for simultaneous, separate or sequential use in the prevention or treatment of an HBV infection or of an HBV-induced disease in mammal in need thereof, wherein said first compound is different from said second compound.

Said first compound is the compound of the application or the pharmaceutical composition of the application, and said second compound is an HBV inhibitor.

Said second compound may e.g., an HBV inhibitor which is chosen from among:
  cytokines having HBV replication inhibition activity, such as interferon, more particularly interferon-alpha,
  substituted sulfonamides having HBV capsid assembly inhibition activity and/or having HBsAg inhibition activity, such as the compounds described in WO 2014033170, WO2014184350, or other combinations (e.g., WO2017181141), or carboxylic acids as described in WO2017140750,
  antiretroviral nucleoside analogues, more particularly reverse transcriptase inhibitors or polymerase inhibitors, such as lamivudine (or 3TC, CAS Registry Number 134678-17-4), adefovir dipivoxil, tenofovir disoproxil fumarate,
  antivirus vaccine or immunological compositions, more particularly anti-HBV vaccine or immunological compositions, and
  the combinations thereof.

More particularly, said second compound may e.g., an HBV inhibitor which is chosen from among:
  substituted sulfonamides having HBV capsid assembly inhibition activity and/or having HBsAg inhibition activity, such as the compounds described in WO 2014033170, WO2014184350, or other combinations (e.g., WO2017181141), or carboxylic acids as described in WO2017140750,
  lamivudine (or 3TC, CAS Registry Number 134678-17-4), adefovir dipivoxil, tenofovir disoproxil fumarate),
  antiviral vaccines and antiviral immunological compositions, more particularly anti-HBV vaccines and anti-HBV immunological compositions, and
  the combinations thereof.

The application also provides pharmaceutically acceptable prodrugs of the compounds of the application, and their use in therapy, more particularly in the treatment or prevention of HBV infection, more particularly of chronic HBV infection. The term "prodrug" is generally intended as a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of the application). A pharmaceutically acceptable prodrug may more particularly be a prodrug that is non-toxic, biologically tolerable, and otherwise biologically suitable for administration to the subject.

The application also provides pharmaceutically acceptable metabolites of the compounds of the application, and their use in therapy, more particularly in the treatment or prevention of a disease or disorder in which the modulation of TLR7 and/or TLR8, more particularly TLR8, is involved, more particularly of HBV infection, more particularly of chronic HBV infection, or in the treatment of cancer.

A pharmaceutically active metabolite generally means a pharmacologically active product of metabolism in the body of a compound of the application or salt thereof.

Prodrugs and active metabolites of a compound may be determined using routine techniques known or available in the art.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the application.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the application, meant as more particularly encompassing the term "consisting of" ("consist(s) of"), and the term "essentially consisting of" ("essentially consist(s) of").

In an attempt to help the reader, the description has been separated in various paragraphs or sections. These separations should not be considered as disconnecting the substance of a paragraph or section from the substance of another paragraph or section. To the contrary, the description encompasses all the combinations of the various sections, paragraphs and sentences that can be contemplated by the person of ordinary skill in the art.

Each of the relevant disclosures of all references cited herein is specifically incorporated by reference. The following examples are offered by way of illustration, and not by way of limitation.

EXAMPLES

TABLE 1

| Abbreviation | Meaning |
| --- | --- |
| rt | Room temperature |
| h | Hour(s) |
| DBU | 1,8-diazabicyclo[5.4.0]undec-7-ene |
| BOP | Benzotriazol-1-yloxy)tris(dimethylamino)phosphonium hexafluorophosphate |
| DMA | N,N-dimethylacetamide |
| DMF | N,N-dimethylformamide |
| EtOAc | Ethyl acetate |
| EtOH | ethanol |

Preparation of Compounds 2-amino-5-bromoquinazolin-4-ol. The title compound was prepared in a procedure analogous to that described for 2-amino-6,7-difluoroquinazolin-4-ol. Rt: 1.16, m/z=240/242 [M+H], Method: G.

(R)-2-((2-amino-5-bromoquinazolin-4-yl)amino)hexan-1-ol. A solution of 2-amino-5-bromoquinazolin-4-ol (2.4 g, 8.68 mmol), D-norleucinol (2.75 g, 23.43 mmol), DBU (3.9 mL, 26.0 mmol) and BOP (4.61 g, 10.42 mmol) in anhydrous DMF (40 mL) was stirred at rt for 2 h and concentrated to give the title product. Rt: 2.16, m/z=339/341 [M+H], Method: D.

(R)-2-((2-amino-5-cyclopropylquinazolin-4-yl)amino)hexan-1-ol (1). A mixture of mixture of (R)-2-((2-amino-5-bromoquinazolin-4-yl)amino)hexan-1-ol (200 mg, 0.59 mmol), cyclopropylboronic acid (151 mg, 1.77 mmol), and potassium phosphate (375 mg, 1.77 mmol), in dioxane (10 mL) and water (0.1 mL), was purged with nitrogen for 10 min. PdCl$_2$(dppf) (38 mg, 0.06 mmol) was added and the mixture and stirred at 100° C. for 18 h. The solids were removed by filtration and the filtrate was concentrated under reduced pressure. The crude was partitioned with ether and water, the organic layer was dried (MgSO$_4$), the solids were removed by filtration, and the solvent of the filtrate was concentrated in vacuo. The mixture was purified by silica column chromatography using a gradient from CH$_2$Cl$_2$ to [CH$_2$Cl$_2$: CH$_3$OH: NH$_3$ (9:1:0.1)].

General Procedure A. A solution of 2-amino-quinazolin-4-ol (2.4 g, 8.68 mmol), D-norleucinol (2 eq), DBU (3 eq.) and BOP (1.3 eq.) in anhydrous DMF was stirred at rt for 2 h and concentrated to give the title product.

2-amino-5-fluoroquinazolin-4-ol. Into a 500 mL autoclave was placed 2-amino-6-fluorobenzoic acid (25 g, 161.16 mmol), EtOH (350 mL), cyanamide (10.16 g, 241.74 mmol) and concentrated HCl (8 mL). The mixture stirred at 80° C. for 16 h, then cooled to rt and the solid was isolated by filtration and washed with ethanol and dried under vacuum. Rt: 0.93, m/z=180 [M+H], Method: H. $^1$H NMR (400 MHz, DMSO-d$_6$) δ ppm 6.98 (m, 1H), 7.13 (d, J=8.3 Hz, 1H), 7.51 (br. s., 2H), 7.64 (m, 1H), 12.30 (br. s, 1H)

(R)-2-((2-amino-5-fluoroquinazolin-4-yl)amino)hexan-1-ol (2). A solution of 2-amino-5-fluoroquinazolin-4-ol (1.07 g, 6 mmol), DBU (1.8 mL, 12 mmol) in anhydrous DMF (30 mL) was stirred at rt under a nitrogen atmosphere. BOP (3.2 g, 7.2 mmol) was added portion wise and stirred for 15 minutes. D-norleucinol (1.41 g, 12 mmol) was added and stirring continued for 2 days. The mixture was poured into ice water and stirred 1 h. The water layer was extracted with EtOAc, the combined organic layers were washed with water and brine. The organic phase was dried over MgSO$_4$, the solids were removed by filtration and the solvent of the filtrate was removed under reduced pressure. The crude was purified via preparatory HPLC (XBridge Prep C18 OBD-10 μm, 50×150 mm, mobile phase: 0.25% NH$_4$HCO$_3$ aq., CH$_3$CN) to afford 0.81 g of the title compound.

5-(trifluoromethyl)quinazoline-2,4-diamine. In a sealed tube, a mixture of 2-fluoro-6-(trifluoromethyl)benzonitrile (4.5 g, 23.8 mmol) and guanidine carbonate (8.57 g, 47.6 mmol) in DMA (54 mL) was stirred at 130° C. for 3 h. The reaction mixture was cooled to rt, diluted with EtOH and the solvent was removed under reduced pressure. The residue was mixed with cold water and the solid was isolated by filtration to give the title compound as a tan solid (5.2 g), and was used in the next step without further purification.

2-amino-5-(trifluoromethyl)quinazolin-4-ol. In a Schlenck flask, a suspension of 5-(trifluoromethyl)quinazoline-2,4-diamine (5.2 g, 0.02 mol) in NaOH (1M, aq., 329 mL) was stirred at 100° C. for 5 h. The pH was adjusted to 2-3 by addition of HCl (1N aq.). The mixture was concentrated in vacuo. Water was added and the solid was isolated by filtration to afford the title product as a white solid (4.25 g). Rt: 1.79 min, m/z=169 [M+H], method I.

(R)-2-((2-amino-5-(trifluoromethyl)quinazolin-4-yl)amino)hexan-1-ol (3). A solution of 2-amino-5-(trifluoromethyl)quinazolin-4-ol (1.5 g, 6.55 mmol), D-norleucinol (2.30 g, 19.6 mmol), DBU (2.94 mL, 19.6 mmol) and benzotriazole-1-yl-oxy-trispyrrolidinophosphonium hexafluorophosphate (PyBOP) (4.43 g, 8.51 mmol) in anhydrous DMF (30 mL) was stirred at rt for 2 h and concentrated to give the title product.

(R)-2-((2-amino-5-(trifluoromethyl)quinazolin-4-yl) amino)hexan-1-ol fumarate. Fumaric acid (346 mg, 2.99 mmol) was added to a solution of (R)-2-((2-amino-5-(trifluoromethyl)quinazolin-4-yl)amino)hexan-1-ol (0.98 g, 2.99 mmol) in $CH_3OH$ (14.3 mL). The resulting solution was stirred at rt for 20 h. The solvent was removed under reduced pressure then dried in vacuo to afford the title compound as a white powder (1.3 g).

(R)-2-((2-amino-7-bromoquinazolin-4-yl)amino)hexan-1-ol. A solution of 2-amino-7-bromoquinazolin-4(3H)-one (3.00 g, 12.5 mmol), D-norleucinol (3.66 g, 31.2 mmol), (DBU) (4.67 mL, 31.2 mmol) and PyBOP (8.45 g, 16.2 mmol) in anhydrous (55 mL) was stirred at rt for 2 h and concentrated to give the title product. Rt: 1.32 min., m/z=339/341 [M+H], method J3.

(R)-2-amino-4-((1-hydroxyhexan-2-yl)amino)quinazoline-7-carbonitrile (4). In a sealed tube, a solution of (R)-2-((2-amino-7-bromoquinazolin-4-yl)amino)hexan-1-ol (1.43 g, 4.22 mmol), $Zn(CN)_2$ (594 mg, 5.06 mmol) and $Pd(PPh3)_4$ (487 mg, 0.422 mmol; 0.1 eq.) in dioxane (31 mL) was degassed by N2 bubbling and was stirred at 100° C. for 16 h. Additional $Zn(CN)_2$ (297 mg; 2.53 mmol) and $Pd(PPh3)_4$ (487 mg, 0.422 mmol) were added, the mixture was degassed with nitrogen and was stirred at 110° C. for 4 h. The reaction mixture was diluted with EtOAc and water. The organic layer was dried over $MgSO_4$, the solids were removed by filtration and the solvent was removed under reduced pressure, then purified by silica gel column chromatography using a mobile phase gradient of $CH_2Cl_2$/$CH_3OH$ (100/0 to 80/20) to give the title compound as a pale orange solid (840 mg).

(R)-2-amino-4-((1-hydroxyhexan-2-yl)amino)quinazoline-7-carbohydrazide. Hydrazine (3.00 mL, 96.4 mmol) was added to solution of methyl (R)-2-amino-4-((1-hydroxyhexan-2-yl)amino)quinazoline-7-carboxylate (1.50 g, 4.71 mmol) in EtOH (30 mL). The solution was heated at 80° C. for 18 h then cooled to rt. The crude was evaporated in vacuo, to give 1.55 g of the title compound as a pale orange solid that was used without further purification in the next step.

(R)-2-((2-amino-7-(1,3,4-oxadiazol-2-yl)quinazolin-4-yl) amino)hexan-1-ol (5). In a Schlenk reactor, a solution of (R)-2-amino-4-((1-hydroxyhexan-2-yl)amino)quinazoline-7-carbohydrazide (1.30 g, 3.88 mmol), triethyl orthoformate (22.8 mL, 137 mmol) and p-toluenesulfonic acid (57 mg, 0.33 mmol) was stirred at 90° C. for 17 h. The reaction mixture was concentrated under reduced pressure. The residue was diluted with EtOAc and washed with $NaHCO_3$ (sat., aq.), water and brine. The organic layer was dried over $MgSO_4$, the solids were removed by filtration, and the solvent of the filtrate was removed under reduced pressure. The crude was purified by reverse phase chromatography (YMC-actus Triart-C18 10 μm 30×150 mm, gradient from 85% aq. $NH_4HCO_3$ 0.2%, 15% ACN to 45% aq. $NH_4HCO_3$ 0.2%, 55% ACN) to give the title product (25 mg)

2-amino-8-methylquinazolin-4-ol. Into a 250 mL round bottom flask equipped with a magnetic stir bar was placed 2-amino-3-methylbenzoic acid (10 g, 66.15 mmol), EtOH (250 mL), cyanamide (4.17 g, 99.2 mmol), and concentrated HCl (3 mL). The mixture stirred at reflux for 6 h. At 1 h intervals, concentrated HCl (0.5 mL) was added via pipette. The reaction mixture cooled to rt and the solids were isolated via filtration and washed with EtOH and dried under vacuum to afford the title compound as an off-white solid (4.8 g). $^1H$ NMR (400 MHz, DMSO-$d_6$) δ ppm 2.41 (s, 3H), 7.15 (t, J=7.5 Hz, 1H), 7.43 (br. s., 2H), 7.55 (d, J=7.0 Hz, 1H), 7.80 (d, J=7.8 Hz, 1H), 11.17-12.49 (m, 1H). Rt: 0.50 min., m/z=176 [M+H], method B.

(R)-2-((2-amino-8-methylquinazolin-4-yl)amino)pentan-1-ol (6). Into a 50 mL glass vial was placed 2-amino-8-methylquinazolin-4-ol (500 mg, 2.71 mmol), anhydrous DMF (10 mL), DBU (1.22 mL, 8.13 mmol), and D-norvalinol (1.40 g, 13.6 mmol). To this solution was added BOP (1.44 g, 3.3 mmol). The vial was sealed and shaken for 15 h at rt. The solvent was removed under reduced pressure. NaOH (1M, aq., 10 mL) was added and washed with EtOAc (5×20 mL). The organic layers were combined, dried ($MgSO_4$), the solids were removed by filtration, and the solvents of the filtrate were removed under reduced pressure. EtOAc was added to the mixture, the product precipitated and was isolated as a white solid (309 mg).

(R)-2-((2-amino-8-methylquinazolin-4-yl)amino)hexan-1-ol (7). Into a 50 mL vial was placed 2-amino-8-methylquinazolin-4-ol (500 mg, 2.24 mmol), anhydrous DMF (10 mL), DBU (1.01 mL, 6.7 mmol), and (R)-(-)-2-amino-1-hexanol (1.32 g, 11.2 mmol). To this solution was added BOP (1.19 g, 2.7 mmol). The vial was sealed and the reaction was shaken 15 h at rt. The solvent was removed under reduced pressure. NaOH (1M, aq., 10 mL) was added and washed with EtOAc (5×20 mL). The organic layers were combined, dried ($MgSO_4$), the solids were removed via filtration, and the solvents of the filtrate were removed under reduced pressure. EtOAc was added to the mixture, and the title compound precipitated as a white solid (161 mg).

2-amino-8-chloroquinazolin-4-ol. Into a 1 L round bottom flask equipped with a magnetic stir bar was placed 2-amino-3-chlorobenzoic acid (25 g, 146 mmol), EtOH (400 mL), cyanamide (9.2 g, 219 mmol), and conc. HCl (5 mL). The mixture is heated to reflux with stirring. At 1 h intervals, conc. HCl (1 mL) was added. At 6.5 h, the heat was removed and the reaction cooled to rt. The solids were isolated by filtration, and washed with EtOH and ether to afford the title compound as a white solid (3.38 g). Rt: 3.37 min., m/z=196 [M+H], method J2.

(R)-2-((2-amino-8-chloroquinazolin-4-yl)amino)hexan-1-ol (8). Into a 50 mL vial was placed 2-amino-8-chloroquinazolin-4-ol (390 mg, 2.0 mmol), anhydrous DMF (10 mL), DBU (0.89 mL, 6.0 mmol), and D-norleucinol (1.17 g, 10.0 mmol). To this solution was added BOP (1.06 g, 2.4 mmol). The vial was sealed and the reaction stirred 15 h at rt. The solvent was removed under reduced pressure. NaOH (1M, aq., 10 mL) was added and washed with EtOAc (5×20 mL). The organic layers were combined, dried (magnesium sulfate), the solids were removed via filtration, and the solvents of the filtrate were removed under reduced pressure. EtOAc was added to the mixture, impurities dissolved and product precipitated out. The supernatant was removed and the process was repeated twice. The remaining solvent was removed under reduced pressure to afford the title compound as a white solid (64 mg).

2-amino-8-fluoroquinazolin-4-ol. 2-amino-3-fluoro-benzoic acid methyl ester (15 g, 88.68 mmol) was dissolved in EtOH (100 mL) in a 250 mL pressure tube, then cyanamide (5.59 g, 133 mmol) and HCl (37% in $H_2O$) were added and the reaction mixture stirred 18 h at 80° C. Upon cooling, a precipitate formed and isolated by filtration, washed with EtOH and dried in vacuo to afford the title compound as a white powder. Rt: 0.44 min., m/z=180 [M+H], method B.

(R)-2-((2-amino-8-fluoroquinazolin-4-yl)amino)hexan-1-ol (9). Into a 50 mL vial was placed 2-amino-8-fluoroquinazolin-4-ol (400 mg, 1.9 mmol), anhydrous DMF (10 mL), DBU (0.83 mL, 5.6 mmol), and D-norleucinol (1.09 g, 9.3 mmol). To this solution was added BOP (0.98 g, 2.2 mmol). The vial was sealed and the reaction shook 15 h at rt. The solvent was removed under reduced pressure. NaOH (1M, aq., 10 mL) was added and washed with EtOAc (5×20 mL). The organic layers were combined, dried (magnesium sulfate), the solids were removed via filtration, and the solvents of the filtrate were removed under reduced pressure. EtOAc was added to the mixture and product precipitated to afford the title compound as a white solid (224 mg).

(R)-2-((2-amino-8-fluoroquinazolin-4-yl)amino)pentan-1-ol (10). Into a 50 mL vial was placed 2-amino-8-fluoroquinazolin-4-ol (400 mg, 1.9 mmol), anhydrous DMF (10 mL), DBU (0.83 mL, 5.6 mmol), and D-norvalinol (766 mg, 7.4 mmol). To this solution was added BOP (0.98 g, 2.2 mmol). The vial was sealed and the reaction shook 15 h at rt. The solvent was removed under reduced pressure. NaOH (1M, aq., 10 mL) was added and washed with EtOAc (5×20 mL). The organic layers were combined, dried (magnesium sulfate), the solids were removed via filtration, and the solvents of the filtrate were removed under reduced pressure. EtOAc was added to the mixture, impurities dissolved and the title product precipitated as a white solid (161 mg).

(R)-2-((2-amino-8-methylquinazolin-4-yl)amino)hexyl isobutyrate (11). (R)-2-((2-amino-8-methylquinazolin-4-yl)amino)hexan-1-ol (2.1 g, 7.65 mmol) was dissolved in DCM (40 mL) and cooled to 0° C. DBU (2.3 mL, 15.3 mmol) was added and the mixture was stirred 30 min. Isobutyrylchloride (1.6 mL, 15.3 mmol) in DCM (10 mL) was added dropwise and the mixture was stirred at rt for 18 h. The mixture was diluted with $CH_2Cl_2$ and washed with water. The organic layer was dried over $MgSO_4$, the solids were removed by filtration and the solvent of the filtrate was removed under reduced pressure. The crude was purified via a silica column using $CH_2Cl_2/CH_3OH$ 100/0 to 95/5 as gradient. The best fractions were evaporated and then dried in vacuo to afford the title compound.

2-amino-5-methoxyquinazolin-4-ol. Into a 1 L round bottom flask equipped with a magnetic stir bar was placed 2-amino-6-methoxybenzoic acid (50 g, 299 mmol), EtOH (400 mL), cyanamide (18.9 g, 448.7 mmol), and conc. HCl (5 mL). The mixture was heated to reflux with stirring and conc. HCl (1 mL) was added at 1 h intervals over the course of 6 h. The reaction cooled to rt and the title compound precipitated, and was isolated as a white solid. $^1$H NMR (400 MHz, DMSO-$d_6$) δ ppm 3.82 (s, 3H), 5.40 (br. s., 1H), 6.77 (m, 1H), 6.84 (m, 1H), 7.23 (br. s., 2H), 7.55 (m, 1H). Rt: 0.89 min, m/z=192 [M+H], method G.

(R)-2-((2-amino-5-methoxyquinazolin-4-yl)amino) hexan-1-ol (12). The title compound was synthesized according to the general procedure A, using 2-amino-5-methoxyquinazolin-4-ol as the starting heterocycle.

2-amino-7-fluoroquinazolin-4-ol. Into a 250 mL round bottom flask equipped with a magnetic stir bar was placed 2-amino-4-fluorobenzoic acid (10 g, 64.46 mmol), EtOH (200 mL), cyanamide (4.06 g, 96.7 mmol), and conc. HCl (3 mL). The mixture stirred at reflux for 6 h. At 1 h intervals, conc. HCl (0.5 mL) was added. The reaction mixture cooled to rt and the solids were isolated via filtration and washed with EtOH and dried under vacuum to afford the title compound as an off-white solid (2.8 g). Rt: 0.49 min, m/z=180 [M+H], method B. $^1$H NMR (400 MHz, DMSO-$d_6$) δ ppm 7.01-7.16 (m, 2H), 7.56 (br. s., 2H), 7.99 (m, 1H), 10.38-13.48 (m, 1H).

(R)-2-((2-amino-7-fluoroquinazolin-4-yl)amino)hexan-1-ol (13). The title compound was synthesized according to the general procedure A, using 2-amino-7-fluoroquinazolin-4-ol as the starting heterocycle. 2-amino-7-methylquinazolin-4-ol. Into a 250 mL round bottom flask equipped with a magnetic stir bar was placed 2-amino-4-methylbenzoic acid (10 g, 64.17 mmol), EtOH (200 mL), cyanamide (4.05 g, 96.3 mmol), and conc. HCl (3 mL). The mixture stirred at reflux for 6 h. At 1 h intervals, conc. HCl (0.5 mL) was added. The reaction mixture cooled to rt and the solids were isolated to afford the title compound as an off-white solid, Rt: 0.50 min, m/z=176 [M+H], method B. $^1$H NMR (400 MHz, DMSO-$d_6$) d ppm 2.43 (s, 3H), 7.22 (d, J=1.0 Hz, 1H), 7.24 (s, 1H), 7.89 (d, J=8.0 Hz, 1H), 8.29 (br. s., 2H), 12.65 (br. s, 1H)

(R)-2-((2-amino-7-methylquinazolin-4-yl)amino)hexan-1-ol (14). The title compound was prepared according to the general procedure A, using 2-amino-7-methylquinazolin-4-ol as the starting heterocycle.

2-amino-6-fluoroquinazolin-4-ol. Methyl 2-amino-5-fluorobenzoate (25 g, 147.8 mmol) was dissolved in EtOH (150 mL) in a 250 mL pressure tube, then cyanamide (9.32 g, 221.7 mmol) and conc. HCl (27 mL) were added and the reaction mixture stirred overnight at 80° C. The reaction cooled to rt, and the title compound was isolated as a white precipitate.

2-amino-5-chloroquinazolin-4-ol. The title compound was prepared in a procedure analogous to that described for 2-amino-6,7-difluoroquinazolin-4-ol. Rt: 3.19 min., m/z=196 [M+H], method J2.

(R)-2-((2-amino-5-chloroquinazolin-4-yl)amino)hexan-1-ol (15). The title compound was prepared according to the general procedure A, using 2-amino-5-chloroquinazolin-4-ol as the starting heterocycle.

2-amino-5-methylquinazolin-4-ol. The title compound was prepared in a procedure analogous to that described for 2-amino-5-chloroquinazolin-4-ol. Rt: 0.17, m/z=[M+H] 176.1, Method: K.

(R)-2-((2-amino-5-methylquinazolin-4-yl)amino)hexan-1-ol (16). The title compound was prepared according to the general procedure A, using 2-amino-5-methylquinazolin-4-ol as the starting heterocycle.

2-amino-3-methoxybenzoic acid methyl ester. A mixture of 2-amino-3-methoxybenzoic acid (6.22 g, 37.21 mmol) and cesium carbonate (18.18 g, 55.81 mmol) in DMF (100 mL) was stirred at rt for 40 min. $CH_3I$ (2.31 mL, 37.21 mmol) in DMF (15 mL) was added and the mixture was stirred at rt overnight. The mixture was diluted with water and extracted with diethyl ether. The aqueous phase was back extracted with diethyl ether. The combined organic extracts were washed with brine, separated, dried over $MgSO_4$, the solids were removed by filtration and the filtrate was concentrated to yield the title compound (5.75 g, 31.73 mmol). LC-MS ES$^+$ m/z=182.1; Rt: 0.68 min, method K.

2-amino-8-methoxyquinazolin-4-ol. A mixture of 2-amino-3-methoxybenzoic acid methyl ester (5.70 g, 41.46 mmol), cyanamide (1.984 g, 47.19 mmol), HCl 37% (1 mL) in EtOH was heated to reflux for 6 h. At 1 h intervals, HCl 37% (0.1 mL) was added. The reaction mixture cooled to rt and the solid was filtered and washed with EtOH to yield 2-amino-8-methoxy-quinazolin-4-ol (2.70 g, 11.86 mmol). LC-MS ES+m/z=192.1; Rt: 0.15 min, method K.

(R)-2-((2-amino-8-methoxyquinazolin-4-yl)amino) hexan-1-ol (17). The title compound was prepared according to the general procedure A, using 2-amino-8-methoxyquinazolin-4-ol as the starting heterocycle.

methyl 2-amino-4-hydroxyquinazoline-7-carboxylate. The title compound was prepared in a procedure analogous to that described for 2-amino-5-chloroquinazolin-4-ol. Rt: 1.02 min, m/z=220 [M+H], method H.

Methyl (R)-2-amino-4-((1-hydroxyhexan-2-yl)amino) quinazoline-7-carboxylate (18). The title compound was prepared according to the general procedure A, using methyl 2-amino-4-hydroxyquinazoline-7-carboxylate as the starting heterocycle.

2-amino-7,8-difluoroquinazolin-4(3H)-one. Dimethylsulfone (13.9 g, 147 mmol) followed by sulfolane (1.15 mL, 12.0 mmol), 2-amino-3,4-difluorobenzoic acid (5 g, 28.9 mmol) and chloroformamidine hydrochloride (6.64 g, 57.8 mmol) were added successively in a sealed tube and the mixture was stirred at 165° C. for 2 h. The resulting solid was added to water and sonicated. The pH was adjusted to 7-8 by the addition of $NH_3$ (aq.). The precipitate was collected by filtration to afford the title compound (5.54 g) as a tan solid. Rt: 1.72 min., m/z=198 [M+H], method J.

(R)-2-((2-amino-7,8-difluoroquinazolin-4-yl)amino) hexan-1-ol (19). The title compound was prepared according to the general procedure A, using methyl 2-amino-7,8-difluoroquinazolin-4(3H)-one as the starting heterocycle.

(R)-2-((2-amino-5-fluoroquinazolin-4-yl)amino)-4-(methylthio)butan-1-ol (20). A solution of 2-amino-5-fluoroquinazolin-4-ol (1 g, 3.964 mmol), DBU (1.183 mL, 7.93 mmol) in anhydrous DMF (20 mL) was stirred at rt under a nitrogen atmosphere. BOP (1.93 g, 4.36 mmol) was added portion wise and stirring continued for 15 min. D-norleucinol (929 mg, 7.93 mmol) was added and stirring continued for 18 h at rt. The solution was purified by preparatory HPLC (Stationary phase: RP XBridge Prep C18 ODB-5 μm, 30×250 mm, Mobile phase: 0.25% $NH_4HCO_3$ aq., $CH_3CN$, $CH_3OH$). (Rt: 0.66 min, m/z=297 [M+H], Method: B)

(2R,3S)-2-((2-amino-5-fluoroquinazolin-4-yl)amino)-3-methylpentan-1-ol (21). A solution of 2-amino-5-fluoroquinazolin-4-ol (200 mg, 1.12 mmol), DBU (0.333 mL, 2.23 mmol) in anhydrous DMF (10 mL) was stirred at rt under a nitrogen atmosphere. BOP (543 mg, 1.23 mmol) was added portion wise and stirring continued for 15 min. L-isoleucinol (162 mg, 1.34 mmol) was added and stirring continued for 18 h at rt. The solution was purified by preparatory HPLC (Stationary phase: RP XBridge Prep C18 ODB-5 μm, 30×250 mm, Mobile phase: 0.25% $NH_4HCO_3$ aq., $CH_3CN$). The desired fractions were collected and evaporated to dryness to afford the title compound as an oil. (Rt: 0.79 min, m/z=279 [M+H], Method: B).

2-amino-4-hydroxy-N-methylquinazoline-5-carboxamide. A 75 mL stainless steel autoclave was sparged with nitrogen and charged with 2-amino-5-bromoquinazolin-4-ol (0.5 g, 2.08 mmol), Pd(OAc)2 (4 mg, 0.02 mmol), 1,3-bis (diphenylphosphino)propane (17 mg, 0.042 mmol), KOAc (408 mg, 4.17 mmol), methylamine (2M in THF, 10 mL), THF (25 mL), and diisopropylethylamine (2 mL). The autoclave was sealed and pressurized to 50 bar CO and heated to 100° C. for 16 h. The solvent was removed and the residue was dissolved in a mixture of $CH_3OH/NH_3$ (7N), then purified by prep HPLC (Stationary phase: RP SunFire Prep C18 OBD-10 μm, 30×150 mm, Mobile phase: 0.25% $NH_4HCO_3$ aq., $CH_3OH$). Rt: 0.78 min, m/z=219 [M+H], method A.

(R)-2-amino-4-((1-hydroxyhexan-2-yl)amino)-N-methylquinazoline-5-carboxamide (22). The title compound was prepared according to the general procedure A, using methyl 2-amino-4-hydroxy-N-methylquinazoline-5-carboxamide as the starting heterocycle.

2-amino-5,7-difluoroquinazolin-4-ol. The title compound was prepared in a procedure analogous to that described for 2-amino-5-chloroquinazolin-4-ol. Rt: 1.01, m/z=198 [M+H], Method: B.

(R)-2-((2-amino-5,7-difluoroquinazolin-4-yl)amino) hexan-1-ol (23). A solution of 2-amino-5,7-difluoroquinazolin-4-ol (200 mg, 1.01 mmol), DBU (0.303 mL, 2.03 mmol) in anhydrous DMF (10 mL) was stirred at rt under a nitrogen atmosphere. BOP (494 mg, 1.12 mmol) was added portion wise and stirring was continued for 15 min. D-norleucinol (162 mg, 1.38 mmol) was added and stirring was continued for 18 h. The mixture was poured into 1 mL water while stirring was continued for 1 h. The solvent was evaporated and the residue was taken in 30 mL $CH_3OH$, stirred and neutralized with conc. HCl. The solution was purified by preparatory HPLC (Stationary phase: RP XBridge Prep C18 ODB-5 μm, 30×250 mm, mobile phase: 0.25% $NH_4HCO_3$ aq., $CH_3OH$).

2-amino-7-(trifluoromethyl)quinazolin-4-ol. The title compound was prepared in a procedure analogous to that described for 2-amino-5-chloroquinazolin-4-ol. Rt: 1.29, m/z=230 [M+H], Method: A.

(R)-2-((2-amino-7-(trifluoromethyl)quinazolin-4-yl) amino)hexan-1-ol (24). The title compound was prepared according to the general procedure A, using 2-amino-7-(trifluoromethyl)quinazolin-4-ol as the starting heterocycle.

(R)-2-amino-4-((1-hydroxyhexan-2-yl)amino)-N,N-dimethylquinazoline-7-carboxamide (32). In a sealed tube, a mixture of methyl (R)-2-amino-4-((1-hydroxyhexan-2-yl) amino)quinazoline-7-carboxylate (1.50 g, 4.71 mmol), dimethylamine (2M in THF, 7 mL) and triazabicyclo[4.4.0]dec-5-ene (TBD) (268 mg, 1.89 mmol) in THF (81 mL) was stirred at 50° C. for 24 h. The solvent was removed under reduced pressure. The crude was purified by reverse phase chromatography (regular C18 25 μm, 120 g YMC ODS-25), Mobile phase gradient: from 70% aq. $NH_4HCO_3$ (0.2%), 30% $CH_3CN$ to 50% aq. $NH_4HCO_3$ (0.2%), 50% MeCN) to afford the title compound as a pale yellow solid (940 mg).

2-amino-5-fluoro-8-methylquinazolin-4-ol. The title compound was prepared in a procedure analogous to that described for 2-amino-5-chloroquinazolin-4-ol. Rt: 1.09, m/z=194 [M+H], Method: A.

(R)-2-((2-amino-5-fluoro-8-methylquinazolin-4-yl) amino)hexan-1-ol (26). The title compound was prepared according to the general procedure A, using 2-amino-5-fluoro-8-methylquinazolin-4-ol as the starting heterocycle.

2-((2-amino-5-fluoroquinazolin-4-yl)amino)-2-methylhexan-1-ol. The titled compound was prepared according to general procedure A. $^1$H NMR (400 MHz, DMSO-$d_6$) δ ppm 0.85 (t, J=6.9 Hz, 3H) 1.05-1.33 (m, 4H) 1.41 (s, 3H) 1.81-2.02 (m, 2H) 3.47 (d, J=10.6 Hz, 1H) 3.66 (d, J=10.6 Hz, 1H) 5.10 (br s, 1H) 6.23 (s, 2H) 6.64-6.83 (m, 2H) 7.00 (dd, J=8.5, 1.0 Hz, 1H) 7.36-7.51 (m, 1H). Rt: 0.92 min., m/z=293 [M+H], Method: B 2-((2-amino-5-fluoroquinazolin-4-yl)amino)-2,4-dimethylpentan-1-ol. The titled compound was prepared according to general procedure A. $^1$H NMR (400 MHz, DMSO-$d_6$) δ ppm 0.88 (dd, J=6.6, 4.0 Hz, 6H) 1.44 (s, 3H) 1.69-1.86 (m, 3H) 1.87-1.92 (m, 2H) 3.49 (d, J=10.6 Hz, 1H) 3.73 (d, J=10.6 Hz, 1H) 6.25 (s, 2H) 6.67 (d, J=18.7 Hz, 1H) 6.71-6.86 (m, 2H) 7.01 (dd, J=8.5, 1.0 Hz, 1H) 7.33-7.52 (m, 1H).

2-((2-amino-5-fluoroquinazolin-4-yl)amino)hexane-1,3-diol. The titled compound was prepared according to general procedure A. Rt: 1.29 min., m/z=295 [M+H], Method: H 2-((2-amino-5-fluoroquinazolin-4-yl)amino)-3-methylhexan-1-ol. The titled compound was prepared according to general procedure A. ¹H NMR (400 MHz, DMSO-d₆) δ ppm 0.82-0.89 (m, 3H) 0.89-0.98 (m, 3H) 1.06-1.50 (m, 4H) 1.73-2.03 (m, 1H) 3.44-3.75 (m, 2H) 4.17-4.43 (m, 1H) 4.74-4.95 (m, 1H) 6.23 (s, 1H) 6.54-6.74 (m, 1H) 6.75-6.85 (m, 1H) 7.03 (dd, J=8.4, 0.9 Hz, 1H) 7.32-7.59 (m, 1H). Rt: 0.87 min., m/z=293 [M+H], Method: B 5-fluoro-N4-(1-methoxyhexan-2-yl)quinazoline-2,4-diamine. The titled compound was prepared according to general procedure A. ¹H NMR (400 MHz, DMSO-d₆) δ ppm 0.83-0.95 (m, 3H) 1.23-1.39 (m, 4H) 1.54-1.69 (m, 2H) 3.29 (s, 3H) 3.36-3.56 (m, 2H) 4.47-4.57 (m, 1H) 6.26 (s, 2H) 6.65 (dd, J=15.4, 8.4 Hz, 1H) 6.73-6.81 (m, 1H) 7.02 (dd, J=8.5, 1.0 Hz, 1H) 7.44 (td, J=8.2, 6.7 Hz, 1H). Rt: 1.02 min., m/z=293 [M+H], Method: B.

2-((2-amino-5-fluoroquinazolin-4-yl)amino)hex-5-en-1-ol. The titled compound was prepared according to general procedure A. ¹H NMR (400 MHz, DMSO-d₆) δ ppm 1.60-1.83 (m, 2H) 2.02-2.20 (m, 2H) 3.51-3.61 (m, 2H) 4.26-4.44 (m, 1H) 4.92-4.97 (m, 1H) 4.99-5.06 (m, 1H) 5.77-6.00 (m, 1H) 6.28 (s, 2H) 6.68-6.87 (m, 2H) 7.03 (dd, J=8.4, 0.9 Hz, 1H) 7.35-7.54 (m, 1H). Rt: 1.49 min., m/z=277 [M+H], Method: A.

TABLE 2

Compounds of formula (I).

| | | | LC-MS | | Melting point | |
| --- | --- | --- | --- | --- | --- | --- |
| | Structure | ¹H NMR | m/z M + H | Method | Rt (min) | (° C.), method | Optical rotation |
| 1 | [structure: 5-cyclopropyl quinazoline-2,4-diamine with (R)-1-hydroxyhexan-2-yl group] | ¹H NMR (300 MHz, CD₃OD) δ 7.39 (m, 1H), 7.17 (d, J = 8.3 Hz, 1H), 7.01 (d, J = 7.4 Hz, 1H), 4.47 (m, 1H), 3.75 (m, 2H), 2.35 (m, 1H), 1.74 (m, 2H), 1.52-1.34 (m, 4H), 1.21 (m, 2H), 1.07 (m, 1H), 0.94 (m, 4H). Exchangeable protons not observed. | 301 | D | 2.28 | 89, A | +0.3° (589 nm, c 0.23 w/v, CH₃OH, 23° C.) |
| 2 | [structure: 5-fluoro quinazoline-2,4-diamine with (R)-1-hydroxyhexan-2-yl group] | ¹H NMR (360 MHz, DMSO-d₆) δ ppm 0.80-0.94 (m, 3 H), 1.23-1.43 (m, 4 H), 1.51-1.71 (m, 2 H), 3.48-3.61 (m, 2 H), 4.34 (br d, J = 3.7 Hz, 1 H), 4.91 (br t, J = 4.9 Hz, 1 H), 6.29 (br s, 2 H), 6.62-6.85 (m, 2 H), 7.02 (d, J = 8.3 Hz, 1 H), 7.44 (td, J = 8.1, 6.8 Hz, 1 H) | 279 | B | 0.80 | 175, B | +11.5° (589 nm, c 0.8 w/v, CH₃OH, 23° C.) |
| 3 | [structure: 5-trifluoromethyl quinazoline-2,4-diamine with (R)-1-hydroxyhexan-2-yl group] | ¹H NMR (400 MHz, DMSO-d₆) δ 7.58-7.65 (m, 1H), 7.52 (m, 2H), 6.51-6.59 (m, 2H), 6.31 (br s, 1H), 4.35 (br s, 1H), 3.47-3.59 (m, 2H), 3.16 (s, 1H), 1.51-1.69 (m, 2H), 1.33 (m, 4H), 0.84-0.90 (m, 3H) | 329 | F | 2.74 | 49, C | +17.69° (589 nm, c 0.26 w/v %, DMF, 20° C.) |

TABLE 2-continued

Compounds of formula (I).

| | Structure | ¹H NMR | LC-MS m/z M + H | Method | Rt (min) | Melting point (° C.), method | Optical rotation |
|---|---|---|---|---|---|---|---|
| 4 | (structure with OH, HN-(R), quinazoline with NC and NH₂) | ¹H NMR (400 MHz, DMSO-d₆) δ 8.24 (m, 1H), 7.49-7.65 (m, 2H), 7.32 (d, J = 8.08 Hz, 1H), 6.32 (br s, 2H), 4.69 (m, 1H), 4.34 (m, 1H), 3.39-3.57 (m, 2H), 1.44-1.87 (m, 2H), 1.29 (m, 4H), 0.85 (br s, 3H) | 286 | F | 2.29 | 222, C | +29.66° (589 nm, c 0.29 w/v %, DMF, 20° C.) |
| 5 | (structure with OH, HN-(R), quinazoline with oxadiazole and NH₂) | Not available | 329 | F | 2.03 | 206, C | +10.4° (589 nm, c 0.25 w/v %, DMF, 20° C.) |
| 6 | (structure with HO, (R), NH, quinazoline with methyl and NH₂) | ¹H NMR (400 MHz, DMSO-d₆) d ppm 0.89 (t, J = 7.3 Hz, 3 H), 1.23-1.43 (m, 2 H), 1.49-1.72 (m, 2 H), 2.37 (s, 3 H), 3.41-3.56 (m, 2 H), 4.31-4.43 (m, 1 H), 4.63-4.70 (m, 1 H), 5.88 (s, 2 H), 6.89 (dd, J = 8.0, 7.2 Hz, 1 H), 7.16 (d, J = 8.4 Hz, 1 H), 7.33 (d, J = 7.0 Hz, 1 H), 7.88 (d, J = 7.9 Hz, 1 H) | 261 | B | 0.64 | | |
| 7 | (structure with HO, (R), NH, quinazoline with methyl and NH₂) | ¹H NMR (400 MHz, DMSO-d₆) d ppm 0.81-0.90 (m, 3 H), 1.20-1.37 (m, 4 H), 1.49-1.61 (m, 1 H), 1.64-1.76 (m, 1 H), 2.37 (s, 3 H), 3.41-3.55 (m, 2 H), 4.34 (td, J = 8.7, 5.3 Hz, 1 H), 4.66 (m, 1 H), 5.88 (s, 2 H), 6.90 m, 1 H), 7.17 (m, 1 H), 7.33 (d, J = 7.0 Hz, 1 H), 7.88 (m, 1 H) | 275 | G | 1.33 | | |

TABLE 2-continued

Compounds of formula (I).

| | Structure | ¹H NMR | LC-MS m/z M + H | Method | Rt (min) | Melting point (° C.), method | Optical rotation |
|---|---|---|---|---|---|---|---|
| 8 | (structure: 8-chloro quinazoline with 2-NH₂, 4-NH-(R)-CH(CH₂OH)-butyl) | ¹H NMR (400 MHz, DMSO-d₆) d ppm 0.78-0.92 (m, 3 H), 1.20-1.40 (m, 4 H), 1.48-1.62 (m, 1 H), 1.63-1.76 (m, 1 H), 3.41-3.56 (m, 2 H), 4.35 (m, 1 H), 4.68 (m, 1 H), 6.25 (br. s., 2 H), 6.96 (m, 1 H), 7.42 (d, J = 8.4 Hz, 1 H), 7.62 (m, 1 H), 8.05 (m, 1 H) | 295 | B | 0.81 | | |
| 9 | (structure: 8-fluoro quinazoline with 2-NH₂, 4-NH-(R)-CH(CH₂OH)-butyl) | ¹H NMR (400 MHz, DMSO-d₆) d ppm 0.80-0.91 (m, 3 H), 1.21-1.38 (m, 4 H), 1.49-1.62 (m, 1 H), 1.65-1.77 (m, 1 H), 3.43-3.56 (m, 2 H), 4.35 (m, 1 H), 4.68 (m, 1 H), 6.20 (br. s., 2 H), 6.94 (m, 1 H), 7.30 (m, 1 H), 7.38 (m, 1 H), 7.89 (m, 1 H) | 279 | B | 0.74 | | |
| 10 | (structure: 8-fluoro quinazoline with 2-NH₂, 4-NH-(R)-CH(CH₂OH)-propyl) | ¹H NMR (400 MHz, DMSO-d₆) d ppm 0.82-0.93 (m, 3 H), 1.19-1.44 (m, 2 H), 1.49-1.59 (m, 1 H), 1.60-1.73 (m, 1 H), 3.42-3.63 (m, 2 H), 4.30-4.50 (m, 1 H), 4.68 (m, 1 H), 6.20 (br. s., 2 H), 6.94 (m, 1 H), 7.29 (m, 1 H), 7.37 (m, 1 H), 7.88 (m, 1 H) | 265 | B | 0.68 | | |

TABLE 2-continued

Compounds of formula (I).

| | Structure | ¹H NMR | LC-MS m/z M + H | LC-MS Method | LC-MS Rt (min) | Melting point (° C.), method | Optical rotation |
|---|---|---|---|---|---|---|---|
| 11 | 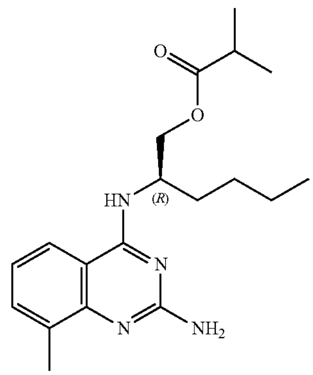 | ¹H NMR (360 MHz, DMSO-d₆) δ ppm 0.81-0.89 (m, 3 H), 1.00 (m, 6 H), 1.22-1.37 (m, 4 H), 1.61 (br d, J = 7.0 Hz, 2 H), 2.37 (s, 3 H), 2.40-2.47 (m, 1 H), 4.03-4.10 (m, 1 H), 4.21 (m, 1 H), 4.63 (m, 1 H), 5.97 (s, 2 H), 6.91 (m, 1 H), 7.36 (m, 2 H), 7.86 (m, 1 H) | 345 | H | 1.95 | | |
| 12 | 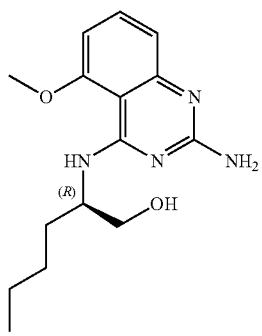 | ¹H NMR (300 MHz, CD₃OD) δ 7.95-8.06 (m, 1H), 6.82-6.94 (m, 2H), 4.40-4.54 (m, 1H), 3.66 (d, J = 5.36 Hz, 2H), 3.31 (br s, 3H), 1.57-1.82 (m, 2H), 1.21-1.47 (m, 4H), 0.91 (br s, 3H). Exchangeable protons not observed. | 291 | D | 2.10 | | +18.8° (589 nm, c 0.82 w/v, CH₃OH, 23° C.) |
| 13 | 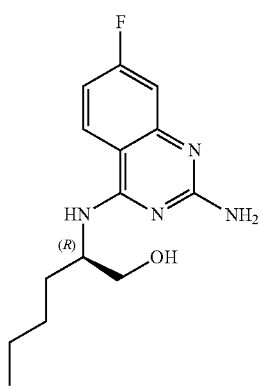 | ¹H NMR (300 MHz, CD₃OD) δ 7.94 (m, 1H), 6.76-6.85 (m, 2H), 4.34-4.43 (m, 1H), 3.57 (d, J = 5.36 Hz, 2H), 1.47-1.72 (m, 2H), 1.29 (br s, 4H), 0.82 (br s, 3H). Exchangeable protons not observed. | 279 | D | 1.97 | 230, A | +38.62° (589 nm, c 0.78 w/v, CH₃OH, 23° C.) |
| 14 | 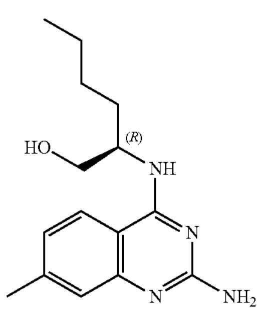 | ¹H NMR (300 MHz, CD3OD) δ 7.83 (d, J = 8.25 Hz, 1H), 7.09 (s, 1H), 6.97 (d, J = 7.70 Hz, 1H), 4.40-4.50 (m, 1H), 3.67 (d, J = 5.36 Hz, 2H), 2.40 (s, 3H), 1.58-1.82 (m, 2H), 1.39 (br s, 4H), 0.85-0.97 (m, 3H). | 275 | D | 2.08 | 227, A | +46.93° (589 nm, c 0.5 w/v, CH₃OH, 23° C.) |

TABLE 2-continued

Compounds of formula (I).

| | Structure | ¹H NMR | LC-MS m/z M + H | Method | Rt (min) | Melting point (° C.), method | Optical rotation |
|---|---|---|---|---|---|---|---|
| | | Exchangeable protons not observed. | | | | | |
| 15 | (structure: 5-chloro-quinazoline with (R)-2-aminohexan-1-ol substituent) | ¹H NMR (300 MHz, CD3OD) δ 7.52 (m, 1H), 7.27 (m, 2H), 4.48 (m, 1H), 3.74 (d, J = 3.9 Hz, 2H), 1.75 (m, 2H), 1.52-1.34 (m, 4H), 0.94 (m, 3H). Exchangeable protons not observed. | 295 | D | 2.15 | | +21.1° (589 nm, c 0.4 w/v, CH₃OH, 23° C.) |
| 16 | (structure: 5-methyl-quinazoline with (R)-2-aminohexan-1-ol substituent) | ¹H NMR (300 MHz, CD3OD) δ 7.62 (t, J = 7.9 Hz, 1H), 7.29-7.20 (m, 2H), 4.57 (m, 1H), 3.77 (m, 2H), 2.87 (s, 3H), 1.76 (m, 1H), 1.51-1.34 (m, 4H), 0.94 (m, 3H). Exchangeable protons not observed. | 275 | D | 2.07 | | +9.5° (589 nm, c 0.72 w/v, CH₃OH, 23° C.) |
| 17 | (structure: 8-methoxy-quinazoline with (R)-2-aminohexan-1-ol substituent) | ¹H NMR (300 MHz, CD3OD) δ 7.79 (dd, J = 7.1, 2.1 Hz, 1H), 7.39 (d, 2H), 4.65 (m, 2H), 4.06 (s, 3H), 3.72 (m, 2H), 1.73 (m, H), 1.40 (m, 4H), 0.92 (m, 3H). Exchangeable protons not observed. | 291 | D | 2.07 | 181, A | +22.6° (589 nm, c 0.6 w/v, CH₃OH, 23° C.) |
| 18 | (structure: 7-methoxycarbonyl-quinazoline with (R)-2-aminohexan-1-ol substituent) | ¹H NMR (400 MHz, DMSO-d₆) δ 8.86 (br s, 1H), 8.46 (m, 1H), 8.00 (s, 1H), 7.86 (m, 1H), 4.87 (s, 1H), 4.45 (m, 1H), 3.92 (s, 3H), 3.54 (m, 2H), 3.14 (m, 2H), 1.62 (br s, 2H), 1.19-1.39 (m, 4H), 0.81-0.91 (m, 3H) | 319 | I | 1.89 | | |

TABLE 2-continued

Compounds of formula (I).

| | Structure | ¹H NMR | LC-MS m/z M + H | LC-MS Method | LC-MS Rt (min) | Melting point (° C.), method | Optical rotation |
|---|---|---|---|---|---|---|---|
| 19 | (structure: 7,8-difluoro-2-aminoquinazolin-4-yl with (R)-2-amino-hexan-1-ol substituent) | ¹H NMR (400 MHz, DMSO-d₆) δ 7.88-8.02 (m, 1H), 7.48 (m, 1H), 6.94-7.08 (m, 1H), 6.41 (br s, 2H), 4.70 (m, 1H), 4.26-4.41 (m, 1H), 3.47 (m, 2H), 1.60 (m, 2H), 1.28 (m, 4H), 0.78-0.90 (m, 3H) | 297 | E | 2.28 | 231, C | +29.31° (589 nm, c 0.29 w/v %, DMF, 20° C.) |
| 20 | (structure: 5-fluoro-2-aminoquinazolin-4-yl with (R)-2-amino-4-(methylthio)butan-1-ol substituent) | ¹H NMR (400 MHz, DMSO-d₆) δ ppm 1.88-1.99 (m, 2 H) 2.05 (s, 3 H) 2.53-2.58 (m, 2 H) 3.55-3.59 (m, 2 H) 4.41 (br s, 1 H) 6.25 (s, 2 H) 6.68-6.85 (m, 2 H) 7.02 (m, 1 H) 7.36-7.52 (m, 1H) | 297 | B | 0.66 | | |
| 21 | (structure: 5-fluoro-2-aminoquinazolin-4-yl with (2R,3S)-2-amino-3-methylpentan-1-ol substituent) | ¹H NMR (400 MHz, DMSO-d₆) δ ppm 0.88 (t, J = 7.5 Hz, 3 H) 0.94 (d, J = 6.8 Hz, 3 H) 1.08-1.22 (m, 1 H) 1.48-1.59 (m, 1 H) 1.76-1.87 (m, 1 H) 3.53-3.67 (m, 2 H) 4.18-4.29 (m, 1 H) 4.72-4.93 (m, 1 H) 6.24 (s, 2 H) 6.66-6.75 (m, 1 H) 6.75-6.83 (m, 1 H) 7.03 (m, 1 H) 7.44 (m, 1 H). | 279 | B | 0.79 | | |
| 22 | (structure: 8-(N-methylcarbamoyl)-2-aminoquinazolin-4-yl with (R)-2-amino-hexan-1-ol substituent) | ¹H NMR (400 MHz, DMSO-d₆) δ ppm 0.77-0.96 (m, 3 H) 1.21-1.36 (m, 4 H) 1.37-1.51 (m, 1 H) 1.66 (m, 1 H) 2.80 (m, 3 H) 3.34-3.42 (m, 2 H) 3.44-3.58 (m, 1 H) 4.10-4.31 (m, 1 H) 4.70 (t, J = 5.1 Hz, 1 H) 6.03 (s, 2 H) 6.94 (m, 1 H) 7.27 (m, 1 H) 7.45 (m, 1 H) 7.70 (m, 1 H) 8.74 (m, 1 H). | 318 | B | 0.61 | | |

TABLE 2-continued

Compounds of formula (I).

| Structure | ¹H NMR | LC-MS m/z M + H | Method | Rt (min) | Melting point (° C.), method | Optical rotation |
|---|---|---|---|---|---|---|
| 23 (5,7-difluoroquinazoline with (R)-hexan-2-ol amino substituent) | ¹H NMR (400 MHz, DMSO-d₆) δ ppm 0.78-0.94 (m, 3 H) 1.20-1.42 (m, 4 H) 1.49-1.72 (m, 2 H) 3.48-3.57 (m, 2 H) 4.26-4.43 (m, 1 H) 4.88 (br s, 1 H) 6.41 (s, 1 H) 6.62-6.71 (m, 1 H) 6.72-6.77 (m, 1 H) 6.79-6.88 (m, 1 H) | 297 | A | 1.68 | | |
| 24 (7-trifluoromethylquinazoline with (R)-hexan-2-ol amino substituent) | ¹H NMR (400 MHz, DMSO-d₆) δ ppm 0.65-0.95 (m, 3 H) 1.18-1.43 (m, 4 H) 1.48-1.60 (m, 1 H) 1.62-1.87 (m, 1 H) 3.50-3.54 (m, 2 H) 4.28-4.48 (m, 1 H) 4.75 (br s, 1 H) 6.63 (s, 2 H) 7.36 (m, 1 H) 7.49 (s, 1 H) 7.92 (m, 1 H) 8.38 (m, 1 H) | 329 | A | 1.69 | | |
| 25 (N,N-dimethylcarboxamide quinazoline with (R)-hexan-2-ol amino substituent) | ¹H NMR (400 MHz, DMSO-d₆) δ 8.11 (m, 1H), 7.37 (d, J = 8.08 Hz, 1H), 7.09 (m, 1H), 6.97 (m, 1H), 6.07 (s, 2H), 4.68 (br s, 1H), 4.34 (m, 1H), 3.47 (m, 2H), 2.99 (s, 3H), 2.90 (br s, 3H), 1.69 (br s, 1H), 1.55 (m, 1H), 1.23-1.37 (m, 4H), 0.85 (br t, J = 5.81 Hz, 3H) | 332 | F | 1.94 | 87, C | +23.2° (589 nm, c 0.25 w/v %, DMF, 20° C.) |
| 26 (5-fluoro-8-methylquinazoline with (R)-hexan-2-ol amino substituent) | ¹H NMR (400 MHz, DMSO-d₆) δ ppm 0.75-0.97 (m, 3 H) 1.19-1.42 (m, 4 H) 1.48-1.75 (m, 2 H) 2.31 (s, 3 H) 3.43-3.62 (m, 2 H) 4.25-4.42 (m, 1 H) 4.86 (t, J = 5.2 Hz, 1 H) 6.20 (br s, 2 H) 6.55-6.82 (m, 2 H) 7.31 (t, J = 7.2 Hz, 1 H) | 293 | A | 1.78 | | |

TABLE 2-continued

Compounds of formula (I).

| | Structure | ¹H NMR | LC-MS m/z M + H | Method | Rt (min) | Melting point (° C.), method | Optical rotation |
|---|---|---|---|---|---|---|---|
| 27 | | | | | | | |
| 28 | | | | | | | |
| 29 | | | | | | | |
| 30 | | | | | | | |
| 31 | | | | | | | |

TABLE 2-continued

Compounds of formula (I).

| | Structure | ¹H NMR | LC-MS m/z M + H | LC-MS Method | Rt (min) | Melting point (° C.), method | Optical rotation |
|---|---|---|---|---|---|---|---|
| 32 | [5-fluoroquinazolin-2-amine with (R)-NH-(S)-CH(CH₂OH)-propyl substituent] | | | | | | |
| 33 | [5-fluoroquinazolin-2-amine with (R)-NH-CH(CH₂OMe)-propyl substituent] | | | | | | |
| 34 | [5-fluoroquinazolin-2-amine with (R)-NH-CH(CH₂OH)-CH₂CH₂CH=CH₂ substituent] | | | | | | |
| | | | | 40 | | | |

Analytical Methods.

TABLE 3

Compounds were characterized by LC-MS using one of the following methods:

| Method code | Instrument | Column | Mobile phase | Gradient | Flow (mL/min) Col T(C) | Run time (min) |
|---|---|---|---|---|---|---|
| A | Waters: Acquity ® UPLC ® - DAD and SQD | Waters HSS T3 (1.8 μm, 2.1 × 100 mm) | A: 10 mM CH₃COONH₄ in 95% H₂O + 5% CH₃CN B: CH₃CN | From 100% A to 5% A in 2.10 min, to 0% A in 0.90 min, to 5% A in 0.5 min | 0.7 55 | 3.5 |
| B | Waters: Acquity ® UPLC ® - DAD and SQD | Waters BEH C18 (1.7 μm, 2.1 × 50 mm) | A: 10 mM CH₃COONH₄ in 95% H₂O + 5% CH₃CN, B: CH₃CN | From 95% A to 5% A in 1.3 min, held for 0.7 min. | 0.8 55 | 2 |
| C | Waters: Acquity ® UPLC ® - DAD and SQD | Waters HSS T3 (1.8 μm, 2.1 × 100 mm) | A: 10 mM CH₃COONH₄ in 95% H₂O + 5% CH₃CN B: CH₃CN | From 100% A to 5% A in 2.10 min, to 0% A in 0.90 min, to 5% A in 0.5 min | 0.8 40 | 3.5 |

TABLE 3-continued

Compounds were characterized by LC-MS using one of the following methods:

| Method code | Instrument | Column | Mobile phase | Gradient | Flow (mL/min) Col T(C) | Run time (min) |
|---|---|---|---|---|---|---|
| D | Agilent 1100 - DAD-MSD G1956A | YMC-pack ODS-AQ C18 (50 × 4.6 mm, 3 μm) | A: 0.1% HCOOH in $H_2O$. B: $CH_3CN$ | From 95% A to 5% A in 4.8 min, held for 1.0 min, to 95% A in 0.2 min. | 2.6<br>35 | 6.0 |
| E | Waters: Acquity ® H-Class - DAD and SQD2 ™ | WatersB EHC18 (1.7 μm, 2.1 × 100 mm) | A: $CH_3COONH_4$ 7 mM 95%/$CH_3CN$ 5%, B: $CH_3CN$ | 84.2% A/15.8% B to 10.5% A in 2.18 min, held for 1.96 min, back to 84.2% A/15.8% B in 0.73 min, held for 0.49 min. | 0.343<br>40 | 6.1 |
| F | Waters: Acquity UPLC ® - DAD and Quattro Micro ™ | Waters BEH C18 (1.7 μm, 2.1 × 100 mm) | A: $CH_3COONH_4$ 7 mM 95%/$CH_3CN$, B: $CH_3CN$ 5% | 84.2% A for 0.49 min, to 10.5% A in 2.18 min, held for 1.94 min, back to 84.2% A in 0.73 min, held for 0.73 min. | 0.343<br>40 | 6.2 |
| H | Waters: Acquity ® UPLC ® - DAD and SQD | Waters: HSS T3 (1.8 μm, 2.1 × 100 mm) | A: 10 mM $CH_3COONH_4$ in 95% $H_2O$ + 5% $CH_3CN$, B: $CH_3CN$ | From 100% A to 5% A in 2.10 min, to 0% A in 0.90 min, to 5% A in 0.5 min | 0.7<br>55 | 3.5 |
| I | Waters: Acquity UPLC ® H-Class - DAD and SQD 2 | Waters HSS ®-T3 (1.8 μm, 2.1 × 50 mm) | A: 95% $CH_3COONH_4$ 7 mM/5% $CH_3CN$, B: $CH_3CN$, C: HCOOH 0.2% in water | 49% A/2% B for 0.25 min, to 8% A/84% B in 1.55 min, held for 1 min, back to 49% A/2% B in 0.2 min, held for 0.8 min. | 0.45<br>40 | 3.8 |
| J | Waters: Acquity UPLC ® H-Class - DAD and QDa | Waters HSS ®-T3 (1.8 μm, 2.1 × 50 mm) | A: 95% $CH_3COONH_4$ 7 mM/5% $CH_3CN$, B: $CH_3CN$, C: HCOOH 0.2% in water | 49% A/2% B for 0.25 min, to 8% A/84% B in 1.55 min, held for 1 min, back to 49% A/2% B in 0.2 min, held for 0.8 min. | 0.45<br>40 | 3.8 |
| J2 | Waters: Alliance ®-DAD - ZQ and ELSD 2000 Alltech | Waters: Xterra MS C18 (3.5 μm, 4.6*100 mm) | A: 25 mM $CH_3COONH_4$ in 95% $H_2O$ + 5% $CH_3CN$ B: CH3CN C: CH3OH D: (40% $CH_3CN$ and 40% $CH_3OH$ and 20% $H_2O$ with 0.25% $CH_3COOH$ | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6<br>40 | 11 |
| J3 | Waters: Acquity UPLC ® H-Class - DAD and SQD 2 | Waters BEH ®C18 (1.7 μm, 2.1 × 50 mm) | A: 95% $CH_3COONH_4$ 7 mM/5% $CH_3CN$, B: $CH_3CN$ | From 95% A to 5% A in 1 min, held for 1.6 min, back to 95% A in 0.2 min, held for 0.5 min. | 0.5<br>40 | 3.3 |

LCMS method K. Analyses were carried out on a Phenomenex Kinetex 00B-4475-AN C18 column (50 mm×2.1 mm I.D.; 1.7 μm) at 60° C. with a flow rate of 1.5 mL/min. A gradient elution was performed from 90% (Water+0.1% HOOH)/10% $CH_3CN$ to 10% (Water+0.1% HOOH)/90% $CH_3CN$ in 1.50 minutes; the resulting composition was held for 0.40 min; then the final mobile phase composition; from 10% (Water+0.1% HOOH)/90% $CH_3CN$ to 90% (Water+

0.1% HOOH)/10% CH₃CN in 0.10 minutes. The injection volume was 2 μL with Agilent autosampler injector or 5 μL with Gerstel MPS injector. MS acquisition range and DAD detector were set to 100-800 m/z and 190-400 nm respectively.

Melting point. Melting points were determined according to the following methods:
A. Mettler Toledo MP50
B. DSC: From 30 to 300° C. at 10° C./min 50 ml N₂
C. DSC: 25° C. to 350° C./10° C. min/40 μl Al
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct. In one instance, the TLR expression construct expresses the respective wild type sequence or a mutant sequence comprising a deletion in the second leucine-rich repeat of the TLR. Such mutant TLR proteins have previously been shown to be more susceptible to agonist activation (U.S. Pat. No. 7,498,409 in the name of Schering Corporation, the content of which is herein incorporated by reference).

HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated 24 h at 37° C. in a humidified 5% C02 atmosphere. Transfected cells were then detached with Trypsin-EDTA, washed in PBS and re-suspended in medium to a density of 1.67×10⁵ cells/mL. Thirty microliters of cells were then dispensed into each well in 384-well plates, where 10 μL of compound in 4% DMSO was already present. Following 6 h incubation at 37° C., 5% CO₂, the luciferase activity was determined by adding 15 μl of STEADY LITE PLUS substrate (PERKIN ELMER) to each well and readout performed on a VIEWLUX ULTRA-HTS microplate imager (PERKIN ELMER). Dose response curves were generated from measurements performed in quadruplicates. Lowest effective concentrations (LEC) values, defined as the concentration that induces an effect which is at least two-fold above the standard deviation of the assay, were determined for each compound.

Compound toxicity has been determined in parallel using a similar dilution series of compound with 30 μL per well of cells transfected with the CMV-TLR7 construct alone (1.67× 10⁵ cells/mL), in 384-well plates. Cell viability has been measured after 6h incubation at 37° C., 5% CO₂ by adding 15 μL of ATP lite (PERKIN ELMER) per well and reading on a ViewLux ultraHTS microplate imager (PERKIN ELMER). Data was reported as $CC_{50}$.

TABLE 4

Biological activity of compounds of formula (I)

| Entry | hTLR7-wt (LEC) | hTLR8-wt (LEC) |
|---|---|---|
| 1 | >100 | 0.35 |
| 2 | 27.7 | 0.07 |
| 3 | >100 | 0.66 |
| 4 | >100 | 0.14 |
| 5 | >25 | 0.38 |
| 6 | >25 | 5.75 |
| 7 | >25 | 0.46 |
| 8 | >25 | 2.72 |
| 9 | >25 | 0.11 |
| 10 | >25 | 3.27 |

TABLE 4-continued

Biological activity of compounds of formula (I)

| Entry | hTLR7-wt (LEC) | hTLR8-wt (LEC) |
|---|---|---|
| 11 | >25 | 0.64 |
| 12 | 11.3 | 0.39 |
| 13 | 29.4 | 0.04 |
| 14 | 11.5 | 0.11 |
| 15 | >100 | 0.07 |
| 16 | >100 | 0.19 |
| 17 | >50 | 3.74 |
| 18 | >100 | 0.57 |
| 19 | >100 | 0.41 |
| 20 | >50 | 0.7 |
| 21 | 1.71 | 0.09 |
| 22 | 2.17 | 1.81 |
| 23 | 6.24 | 0.04 |
| 24 | 3.36 | 0.35 |
| 25 | >100 | 3.89 |
| 26 | >100 | 0.57 |

The invention claimed is:

1. A compound of formula (I)

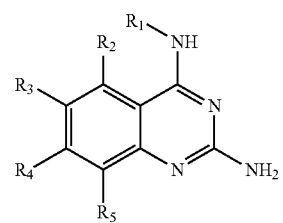

or a pharmaceutically acceptable salt or solvate thereof, wherein $R_1$ is of formula (II):

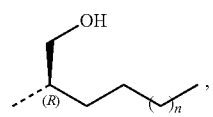

formula (II)

wherein n is 0, 1, or 2;
or of formula (III):

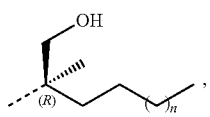

formula (III)

wherein n is 0, 1, or 2, the carbon of $R_1$ bonded to the amine in the 4-position of the quinazoline is in (R)-configuration, $R_2$ is hydrogen, deuterium, fluorine, chlorine, methyl, methoxy, cyclopropyl, trifluoromethyl, or carboxylic amide, wherein each of methyl, methoxy and cyclopropyl is optionally substituted by one or more substituents independently selected from fluorine and nitrile, R₃ is hydrogen or deuterium, R₄ is hydrogen, deuterium, fluorine, methyl, carboxylic ester, carboxylic amide, nitrile, cyclopropyl, C₄₋₇heterocycle, or 5-membered heteroaryl group, wherein each of methyl, cyclopropyl, C₄₋₇heterocycle and 5-membered heteroaryl group is optionally substituted by one or more substituents independently selected from fluorine, hydroxyl, or methyl, and R₅ is hydrogen, deuterium, fluorine, chlorine, methyl, or methoxy, provided that at least one of R₂, R₃, R₄ and R₅ is not hydrogen.

2. The compound of claim 1 or a pharmaceutically acceptable salt or solvate thereof, wherein R₁ is of formula (II):

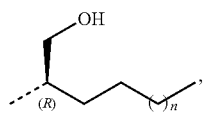

wherein n is 0, 1, or 2.

3. The compound of claim 1 or a pharmaceutically acceptable salt or solvate thereof, wherein R₂ is fluorine, chlorine or methyl, and wherein methyl is optionally substituted by one or more substituents independently selected from fluorine and nitrile.

4. The compound of claim 1 or a pharmaceutically acceptable salt or solvate thereof, wherein R₂ is fluorine or chlorine.

5. The compound of claim 1 or a pharmaceutically acceptable salt or solvate thereof, wherein R₄ is fluorine or methyl, and wherein methyl is optionally substituted by one or more substituents independently selected from fluorine, hydroxyl, or methyl.

6. The compound of claim 1, which is chosen from among compounds 1-34:

-continued
| Compound number | |
|---|---|
| 8 | 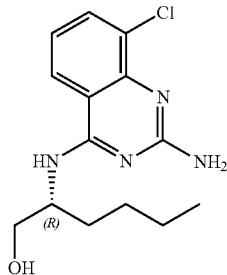 |
| 9 | 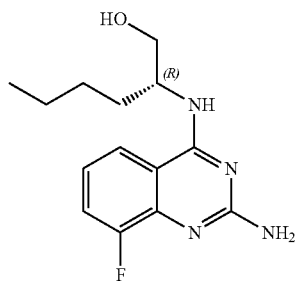 |
| 10 | 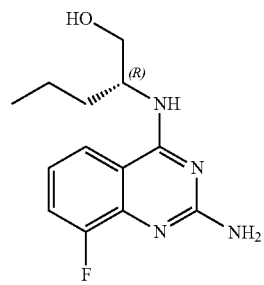 |
| 11 | 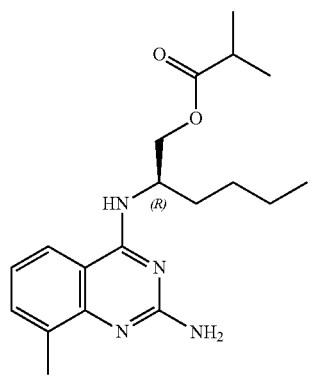 |
| 12 | 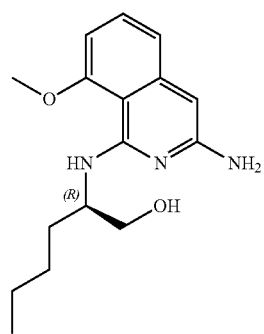 |
-continued
| Compound number | |
|---|---|
| 13 | 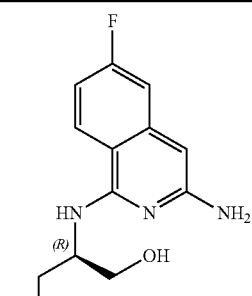 |
| 14 | 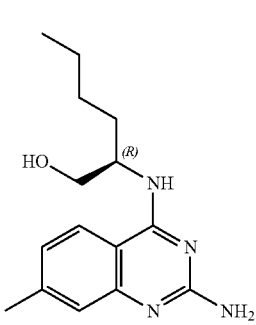 |
| 15 | 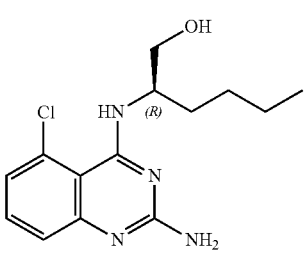 |
| 16 | 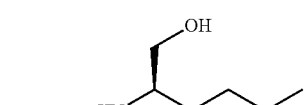 |
| 17 | 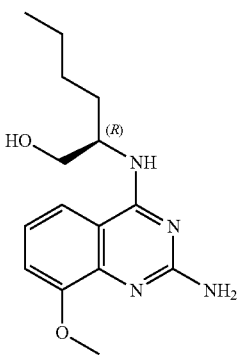 |

| Compound number | | Compound number | |
|---|---|---|---|
| 18 | 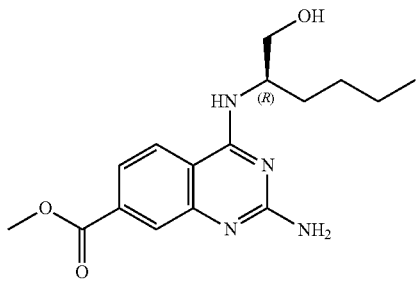 | 24 | 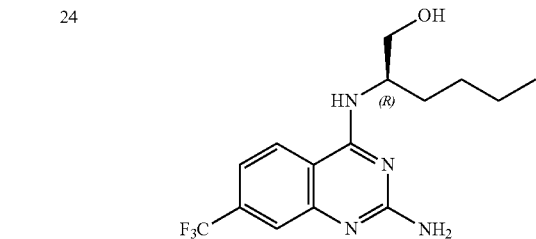 |
| 19 | 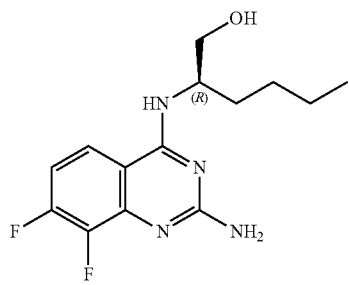 | 25 | 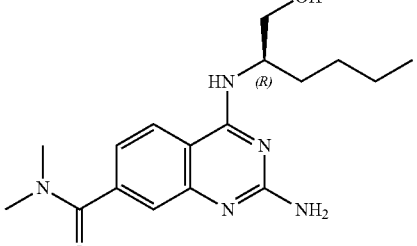 |
| 20 | 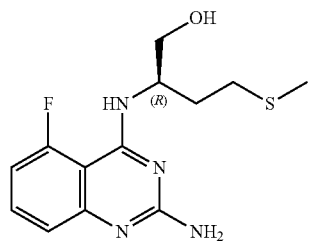 | 26 | 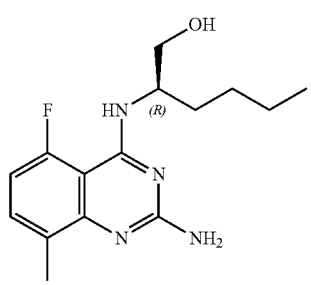 |
| 21 | 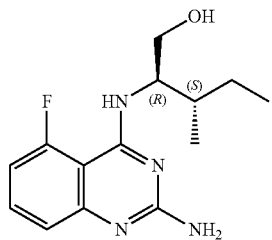 | 27 | 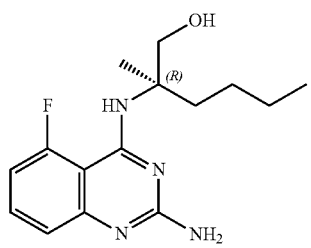 |
| 22 | 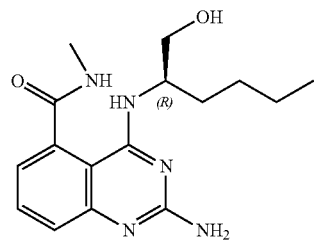 | 28 | 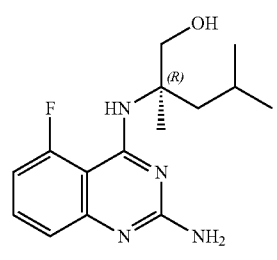 |
| 23 | 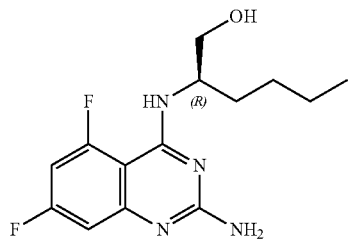 | 29 | 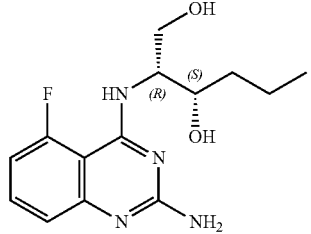 |

-continued

| Compound number | |
|---|---|
| 30 | 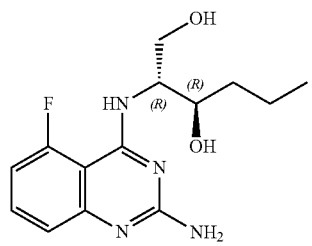 |
| 31 | 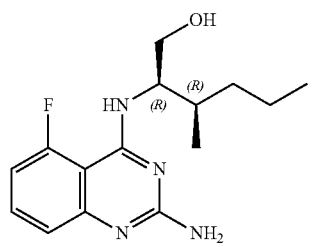 |
| 32 | 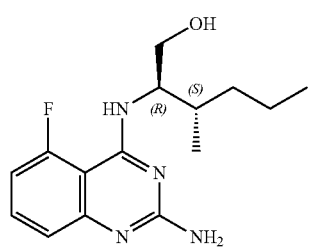 |
| 33 | 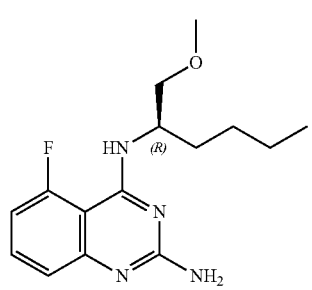 |
| 34 | 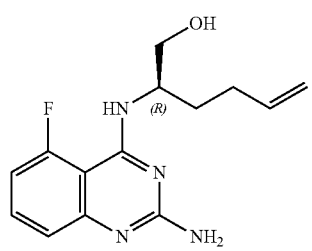 | or a pharmaceutically acceptable salt or solvate thereof.

7. The compound of claim 6, which is chosen from among compounds 1, 2, 3, 4, 5, 7, 9, 11, 12, 13, 14, 15, 16, 18, 19, 20, 21, 22, 23, 24 and 26 or a pharmaceutically acceptable salt or solvate thereof.

8. The compound of claim 6, which is chosen from among compounds 2, 13, 14, 15, 16, 21 and 23 or a pharmaceutically acceptable salt or solvate thereof.

9. The compound of claim 6, wherein the compound is:

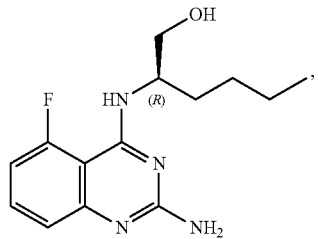

or a pharmaceutically acceptable salt or solvate thereof.

10. The compound of claim 6, wherein the compound is:

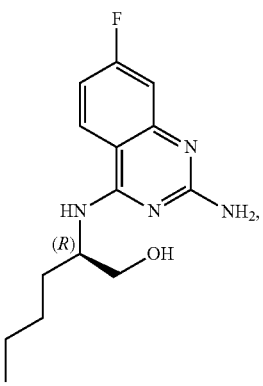

or a pharmaceutically acceptable salt or solvate thereof.

11. The compound of claim 6, wherein the compound is:

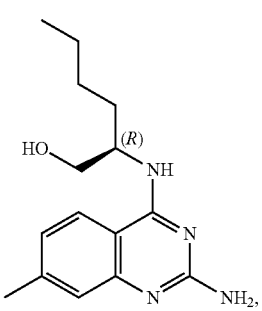

or a pharmaceutically acceptable salt or solvate thereof.

12. The compound of claim 6, wherein the compound is:

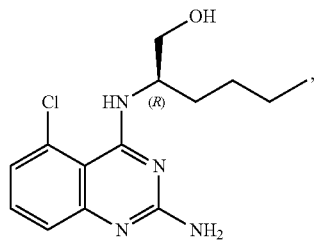

or a pharmaceutically acceptable salt or solvate thereof.

13. The compound of claim 6, wherein the compound is:

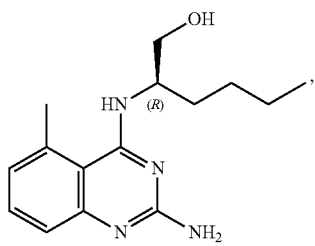

or a pharmaceutically acceptable salt or solvate thereof.

14. The compound of claim 6, wherein the compound is:

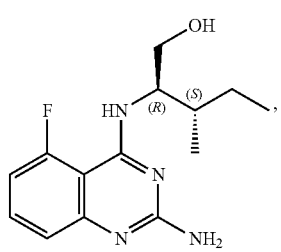

or a pharmaceutically acceptable salt or solvate thereof.

15. The compound of claim 6, wherein the compound is:

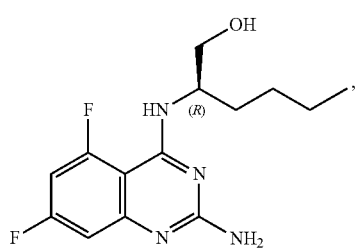

or a pharmaceutically acceptable salt or solvate thereof.

16. The compound of claim 1 or a pharmaceutically acceptable salt or solvate thereof, which is a TLR8 agonist, and which displays improved TLR8 agonism over TLR7.

17. The compound of claim 1 or a pharmaceutically acceptable salt or solvate thereof, which stimulates or activates a Th1 immune response, and/or which stimulates or activates cytokine production.

18. A pharmaceutical composition, which comprises the compound of claim 1 or a pharmaceutically acceptable salt or solvate thereof, together with one or more pharmaceutically acceptable excipients, diluents or carriers.

19. A method of agonizing TLR-8 receptors in a subject suffering from a viral infection or a virus-induced disease, comprising administering an effective amount of the compound of claim 1 or a pharmaceutically acceptable salt or solvate thereof to the subject in need thereof.

20. A method of treating a chronic viral infection in a subject in need thereof, comprising administering an effective amount of the compound of claim 1 or a pharmaceutically acceptable salt or solvate thereof to the subject in need thereof, thereby agonizing TLR 8 receptors in the subject.

21. The method of claim 20, wherein the chronic viral infection Of is a HBV infection.

22. The method of claim 21, wherein the compound is selected from the group consisting of:

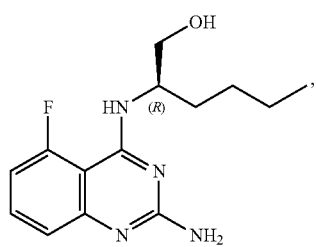

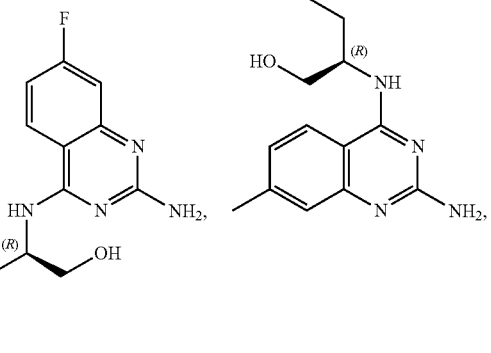

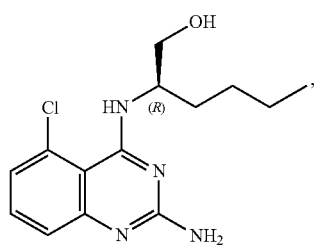

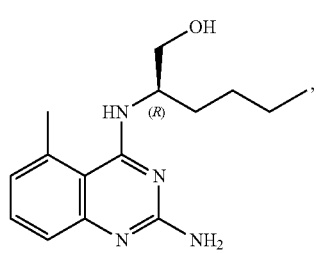

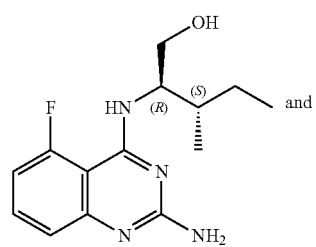

and

-continued

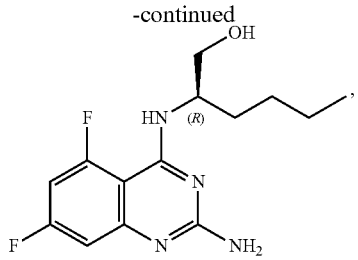

or a pharmaceutically acceptable salt or solvate thereof.
23. The method of claim 21, wherein the compound is:

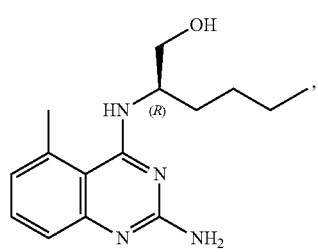

or a pharmaceutically acceptable salt or solvate thereof.
24. The method of claim 23, wherein the method further comprises administering a second compound for treatment of an HBV infection.
25. The method of claim 21, wherein the compound is:

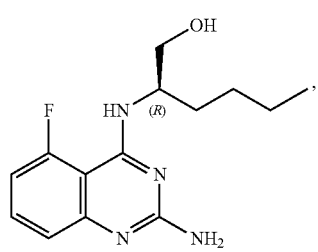

or a pharmaceutically acceptable salt or solvate thereof.
26. The method of claim 25, wherein the method further comprises administering a second compound for treatment of an HBV infection.
27. The method of claim 21, wherein the compound is:

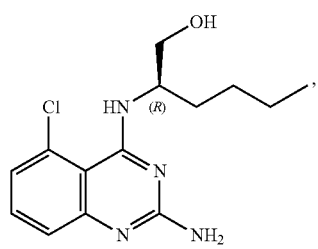

or a pharmaceutically acceptable salt or solvate thereof.
28. The method of claim 27, wherein the method further comprises administering a second compound for treatment of an HBV infection.
29. The method of claim 21, wherein the method further comprises administering a second compound for treatment of an HBV infection.

30. The method of claim 20, wherein the compound is selected from the group consisting of:

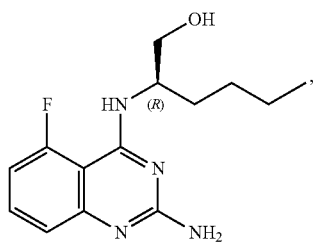

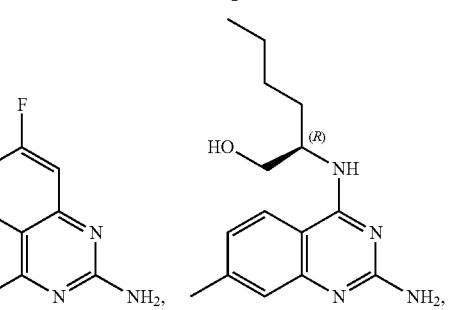

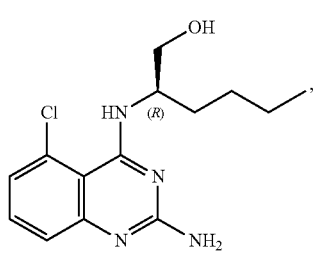

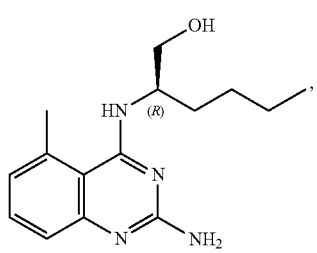

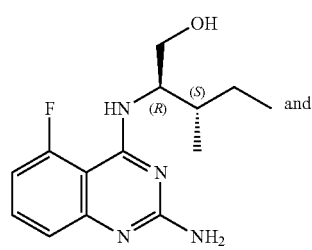 and

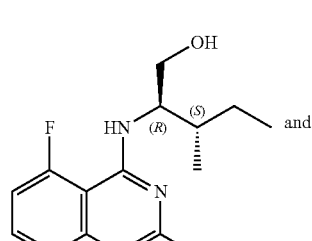

-continued

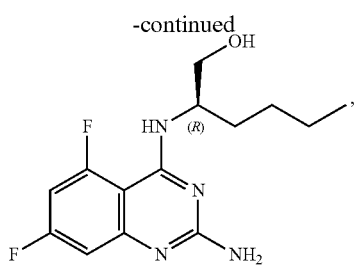

or a pharmaceutically acceptable salt or solvate thereof.

31. The method of claim 20, wherein the compound is:

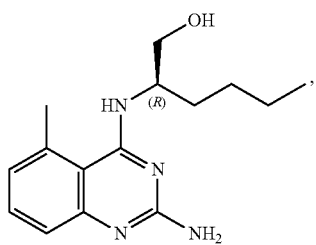

or a pharmaceutically acceptable salt or solvate thereof.

32. The method of claim 20, wherein the compound is:

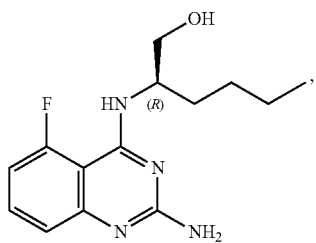

or a pharmaceutically acceptable salt or solvate thereof.

33. The method of claim 20, wherein the compound is:

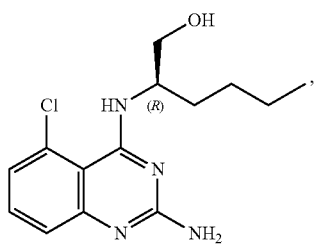

or a pharmaceutically acceptable salt or solvate thereof.

34. The compound of claim 1 or a pharmaceutically acceptable salt or solvate thereof, wherein $R_1$ is of formula (II) and n is 1.

35. The compound of claim 34 or a pharmaceutically acceptable salt or solvate thereof, wherein $R_2$ is fluorine.

36. The compound of claim 34 or a pharmaceutically acceptable salt or solvate thereof, wherein $R_4$ is fluorine or methyl, and wherein methyl is optionally substituted by one or more substituents independently selected from fluorine, hydroxyl, or methyl.

37. A method of selectively agonizing TLR 8 over TLR 7 in a subject in need thereof, comprising administering an effective amount of the compound of claim 1 or a pharmaceutically acceptable salt or solvate thereof to the subject in need thereof, thereby agonizing TLR 8 receptors in the subject.

38. The method of claim 37, wherein the compound is:

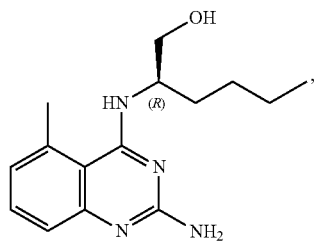

or a pharmaceutically acceptable salt or solvate thereof.

39. The method of claim 37, wherein the compound is:

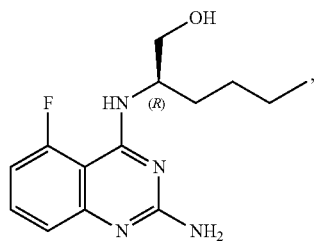

or a pharmaceutically acceptable salt or solvate thereof.

40. The method of claim 37, wherein the compound is:

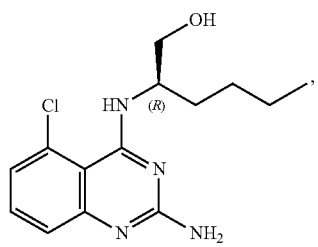

or a pharmaceutically acceptable salt or solvate thereof.

* * * * *